United States Patent [19]

Davis et al.

[11] Patent Number: 5,386,038
[45] Date of Patent: Jan. 31, 1995

[54] WATER TREATMENT AGENT

[75] Inventors: Keith P. Davis; Peter A. T. Hoye, both of Stourbridge; Michael J. Williams, Bridgnorth; Gary Woodward, Kidderminster; Martin P. Greenhall, Northfield, all of England

[73] Assignee: Albright & Wilson Limited, West Midlands, England

[21] Appl. No.: 947,094

[22] Filed: Sep. 17, 1992

Related U.S. Application Data

[63] Continuation-in-part of Ser. No. 809,960, Dec. 18, 1991, abandoned.

[30] Foreign Application Priority Data

| Dec. 18, 1990 | [GB] | United Kingdom | 9027357 |
| May 8, 1991 | [GB] | United Kingdom | 9109861 |
| Nov. 6, 1991 | [GB] | United Kingdom | 9123501 |
| Jun. 16, 1992 | [GB] | United Kingdom | 9212748 |

[51] Int. Cl.$^6$ ............................................ C07D 307/36
[52] U.S. Cl. ................................. 549/262; 562/20
[58] Field of Search ............................. 549/262; 562/20

[56] References Cited

U.S. PATENT DOCUMENTS

| 2,724,718 | 11/1955 | Stiles et al. | 260/461 |
| 2,957,931 | 10/1960 | Hamilton et al. | 260/403 |
| 3,743,688 | 7/1973 | Nicholson et al. | 260/970 |
| 3,755,504 | 8/1973 | Nicholson et al. | 260/932 |
| 4,046,707 | 9/1977 | Smith et al. | 252/180 |
| 4,183,879 | 1/1980 | Battiste | 260/932 |
| 4,351,796 | 9/1982 | Marshall | 422/15 |
| 4,590,014 | 5/1986 | Wolf et al. | 260/502.4 |

FOREIGN PATENT DOCUMENTS

| 0360747 | 3/1990 | European Pat. Off. |
| 0479465 | 4/1992 | European Pat. Off. |
| 3044214 | 6/1982 | Germany |
| 3142517 | 5/1983 | Germany |
| 660918 | 11/1951 | United Kingdom |
| 694772 | 7/1953 | United Kingdom |
| 1334365 | 10/1973 | United Kingdom |
| 1458235 | 12/1976 | United Kingdom |

OTHER PUBLICATIONS

Journal of the American Chemical Society, 92:6, Mar. 25, 1970, pp. 1685–1687.
Kogyo Kayaka Zasshi, 68, 11 (1965) (translation only).

Primary Examiner—Paul J. Killos
Attorney, Agent, or Firm—Frishauf, Holtz, Goodman & Woodward

[57] ABSTRACT

Unsaturated compounds which can be dissolved in aqueous based solvents, such as ethylenic or acetylenic carboxylate or alcohols with less than 10 carbon atoms, especially maleic and/or acrylic acid or propargyl alcohol, are reacted with alkali metal phosphite in aqueous solution at neutral or alkaline pH in the presence of free radical initiators such as persulphate to form threshold scale and corrosion inhibitors.

3 Claims, 2 Drawing Sheets

WATER TREATMENT AGENT

This application is a Continuation-In-Part, of application Ser. No. 07/809,960, filed Dec. 18, 1991, abandoned.

The present invention relates to a novel method of phosphonation which is particularly useful for the preparation of water treatment agents that inhibit scale formation and/or corrosion of metal, e.g. iron, surfaces by aqueous systems, such as boiler water. The invention relates especially to certain novel agents which are effective when present in very low concentrations e.g. 0.1 to 100 ppm.

Such agents, on account of the minimum concentrations required for effective action, are known as threshold agents. The threshold levels are tiptcally very much lower than would be required to achteve useful protection by a stoichtometric reagent such as a classical chelatlng agent.

While a large number of threshold agents are known, some of which are both scale inhibitors and corrosion inhibitoPs the most effective and commercially acceptable scaling inhibitors are relatively ineffective, and are not used commercially, as corrosion inhibitors and vice versa. One group of compounds, which has been reported to show scale and corrosion inhibiting properties, is phosphonosuccintc acid and its salts. These are not, however, sufficiently effective to have enjoyed significant commercial success. The compound has been fairly expensive to make by the conventional route, which entails reacting a diester of maleic acid with dimethyl phosphite to form a phosphonosuccinic ester intermediate. lhe intermediate is then hydrolysed.

A particularly successful class of scale inhibitors is 2-phosphono-1,2,4-tricarboxybutane and its salts which will be referred to collectively herein as "PTCB". This is prepared by reacting the above described phosphonosuccintc ester intermediate with methyl acrylate to form the ester of the desired product, which must then be hydrolysed. Ths is a very expensive process on account both of the cost of the reagents and the number of steps involved. Nevertheless it has been commercially successful in competition with much cheaper products because it is effective in particularly low concentration and is said to be useful in the treatment of certain problem water systems, which cannot be effectively treated by other scale inhibitors. PTCB is not, however, normally used commercially as a corrosion Inhibitor.

The most cost effective and commercially successful organic corrosion inhibitors in current use are 2-hydrog-phosphonoacetic acid, (HO)$_2$ PO CHOH.COOH, and its salts, hereinafter collectively referred to as HPP. HPP has some major drawbacks as a corrosion inhibitor, in that it is relatively ineffective in the presence of zinc, which is widely used in water treatment, and in chlorjnated water systems. It is not very effective as a scale inhibitor.

The phosphonation of water-insoluble long chain olefins in a non-aqueous solvent, wth phosphorous acld and a free radical catalyst, has been known since 1965 from a paper by Yoshiki Okamoto and Hirosh Sakurai in Kogyo Kyaka Zassht 68, 11 (1965). The products have no been reported to be useful as corrosion or scaling nhtbitors.

Attempts to phosphonae more reactive, water-soluble olerins such as acrylic or maleic acid with phosphorous have given negligible yields of phosphonated products.

GB 1458235 describes the preparation of certatn scale inhibitors based on similar chemistry to the Japanese paper. The products are prepared, typically, by reacting hypophosphorous acid with acryllc acid. However two examples, namely examples H and I, describe an alleged reaction of phosphorous acid with acrylic acid, in the presence of a catalytic amount of potassium persulphate. The products are not specifically identified but it is implied, on the basis of their phosphorus analysis, that they are phosphonted oltgomers of acrylic acid. The performances of these reaction products as scale inhibitors are mentioned in the Table 1 on p. 6 of the patent. This Table shows that they are markedly inferior to the other examples of the invention quoted in the Table and indeed not significantly more effective than conmmrcial polyacrylic acid which is quoted as a comparative example.

The latter observation is, in fact, easily explained. We have repeated examples H and I of GB 1458235 and discovered that the reaction product is in fact polyacrylic acid. NMR confirms the absence of any P-C bonds. Presumably the Patentee had failed to remove all inorganic impurities before conducting its analysis.

The failure of phosphorous acid to give useful yields of effective phophonated water treatment agents with unsaturated carboxyltc acids, has led to the abandonment of this approach and reliance instead on the costly multi stage routes using phosphate esters and carboxylate esters.

There are many references in the art to the use of phosphono carboxyltc acids in water treatment and to their preparation starting from alkylphosphites. They include U.S. Pat. Nos. 2,478,390, 2,957,931, 3,923,876, 3,959,168, 4,042,324, 4,057,511, 4,351,796 and DE-A-3,044,214.

One class of organophosphonic compounds, which have not hitherto been accessible except by very expensive multi stage syntheses of no commercial interest, and whose potentialities have therefore been overlooked, are the vicinal dtphosphonites. It has been proposed to make 2,3-diphosphono proptonic acid by preparing the trtethyl ester of 2-phosphonoacettc acid and reactlng it with triethyl phosphtte and formaldehyde. The resulting ester is then saponifled. The starting ester is an expensive chemical curiously which is not readily available, and the subsequent preparetire steps add substantially to the cost of the product. It has also been proposed to synthesise 2,3-diphosphonobuta-1,4-dioic acid by reacting the tetraethyl ester of phosphonomalelc acid with diethyl phosphite in the presence of a base and hydrolysing the resulting este. Again the cost of the reagents and of the ensuing steps is prohibitive.

We have now discovered that lower molecular weight (e.g. less than 10 carbon atom) olefins and acetylenes, especially water soluble hydroxy oleflns and acetylenes and salts of carboxy olefins and acetylenes such as alkali metal salts, (e.g. propyolates, acrylates and/or maleates or allyl or propargyl alcohol) react with water soluble phosphites in aqueous solution, usually at elevated temperatures, in the presence of free radicals to form high yields of novel products which are generally very much cheaper to make than conventional phosphonated products such as PTCB and yet are at least comparable to the latter, and in some cases superior, in performance as scale inhibitors.

Moreover the products are also highly effective as corrosion inhibitors, especially in the presence of calcium ion. They are in many cases substantially superior to HPP in the presence of chlorine and of the hypochlorite or hypobromite commonly present in chlorineted water systems and/or in the presence of chlorine dioxide. The products are also more effective as corrosion inhibitors than HPP in the presence of zinc ions.

Particularly preferred are the reaction products obtained with maleares, acrylates or mixtures thereof, or propargyl alcohol. In the case of maleares, the product is generally a mixture of a phosphonosuccinate salt with peviously unreported components which we believe include members of the homologous series of the general formula $H(CHCO_2M.CHCO_2M)_n PO_3M_2$ wherein n usually has an average value of 2 to 5 and 14 is a cation. Typically the mixture may comprise a phosphonosuccinate (n-1) and a substantial proportion of the higher homologues. It is also possible that hydroxy and/or sulphate substituted oligomers are formed. The mixture usually contains a small proportion of phosphate.

We have also discovered that acetylenic compounds and especially wate soluble acetylentc alcohols and carboxylate salts, react with phosphite salts in the pesece of free radical initiators especially persulphates, to form a range of vicihal diphosphono compounds which are of value as scaling and corrosion inhibitors.

In particular we have discovered that propargyl alcohol and its homologs react with alkali metal phosphites in the presence of, e.g., persulphates to form novel compounds which combine good scale inhibiting properties with good inhibition of corrosion especially in calcium containing systems.

According to the present invention either the product of the foregoing reaction or any of its novel components, e.g. oligomers of the above formula, may be used as scaling inhibitors or as corrosion inhibitors.

Figure 1:
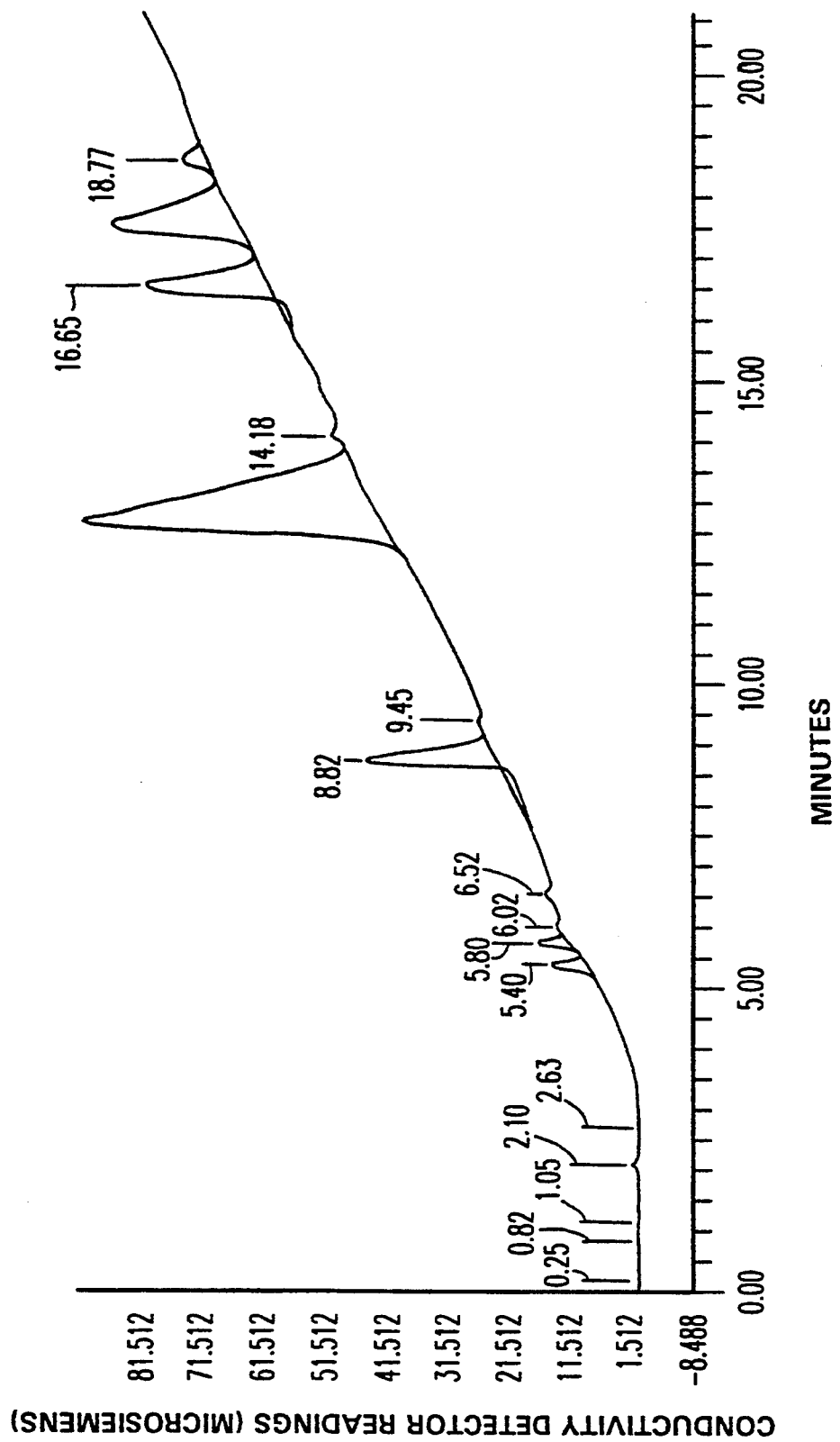
FIG. 1 shows an ion chromatograph of the product of Example 1 showing the change in conductivity measured by the conductivity detector in microsiemens, versus time (minutes).

According to a first embodiment the invention provides a method of phosphonating a preferably water-soluble or sparingly water soluble, active, ethylenically or acetylentcally unsaturated compound by reacting it with a water soluble phosphite salt in the presence of sufficient of a solvent, capable of dissolving both reagents, to dissolve at least part of the reaction mixture, and of sufficient free radical to convert a substantial proportion of said unsaturated compound to a phosphonated derivative. Preferably the solvent is an aqueous based solvent.

The term "active, unsaturated compound includes ethylenically and acetylenically unsaturated compounds in which the unsaturated bond is activated by the proximity of at least one hydroxyl, carbonyl, carboxylate, sulphonate and/or phosphonate group or by inclusion tn a strained ring. Preferred examples include alkali metal maleares, acrylates, proptolates, butyne-1,4 dioates butyne-1, 4-diol, propargyl alcohol, vnyl sulphonate, vtnyl phosphonate, allyl alcohol, norbornene and cyclopentadiene.

Thus according to a second embodiment, the invention provides a method for the preparation of scaling and/or corrosion inhibitors which comprises heating: (1) at least one water soluble carboxy, hydoxy, sulphono or phosphono olefin having the general formula $RZC-CR_2$ where at least one R group is a COOH, $CH_2OH$, $SO_3M$ or $PO_3M_2$ group and each of the other R groups may be the same or different and each represents hydrogen or a hydrocarbon or substituted hydrocarbon group, or in which two of the R groups together form a cycloalkyl or cycloalkenyl group, or part thereof, and M is a cation such that the salt is water soluble with (2) a waer soluble salt of phosphorous acid; in the presence of (3) sufficient of an aqueous based solvent to dissolve at least part of each of the reagents; and (4) sufficient free radicals to form a phosphonated oligomer of said olefin.

According to a third embodiment our invention provides a method of preparing vicinal diphosphono compounds which comprises reacting an acetylenic compound with a phosphite salt in the presence of sufficient free radical to convert a substantial proportion of said acetylenic compound to a vicinal disphosphono compound, preferably in an aqueous based solution.

Preferably the acetylentc compound is water soluble, e.g, an acetylenic alcohol or carboxylate salt, especially one having less than 10, more particularly less than 6, e.g. less than 5 carbon atoms. We have found that propargyl alcohol reacts according to our invention to give a particularly effect}ve and novel combined scaling and corrosion inhibttor, namely 2,3-diphosphonopropanol, usually formed in admixture with some phosphonated oligomers of propargyl alcohol. Other novel and useful compounds whlch may be prepared by the method of our invention and which are included in our invention comprise compounds of the formula.

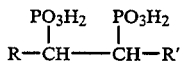

Where R is a hydroxy and/or carboxy substituted alkyl group having a total of 1 to 5 carbon atoms and R' is hydrogen, a carboxylate group, a hydrocarbon group having from 1 to 4 carbon atoms or an R group, and their salts. Preferably the compound has a total of less than six carbon atoms.

The invention according to a fourth embodiment provides novel phosphonated oligomers of active olefins which oligomers have the formula

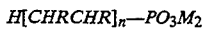

wherein at least one R group in each unit is a COOM, $CH_2OH$, sulphono or phosphono group and the other R group which may be the same as, or different from, the first R group, is hydrogen or a COOM, hydroxyl, phosphono, sulphono, sulphato, $C_{1-7}$alkyl, $C_{1-7}$alkenyl group or a carboxylate, phosphono, sulphono, sulphato and/or hydroxy substituted $C_{1-7}$alkyl or $C_{1-7}$alkenyl group, and each M is a cation such that the phosphonated oligomer is water soluble and n is greater than 1, e.g. up to 6. Preferably n has value less than 5 e.g. 1.2 to 3.

This invention also provides phosphonated cooltgimers of the above formula, but in which the $[CHRCHR]_n$ chain contains at least two [CHRCHR] groups derived from different monomers and in which n has a total value of at least 3. For example we include a phosphonated trimer or higher cooligomer of maleate and acrylate containing at least one [CH$_2$ CHCOOH] and at least one [CHCOOH CHCOOM] group.

The invention, according to a preferred embodiment, provides a novel phosphonated oligomer or mixture of phosphonated oligomers of maleic acid, of the formula H(CHCO$_2$M.CHCO$_2$M)$_n$PO$_3$M$_2$ where n is greater than 1 and M is a cationic species such that the compound is water soluble, and especially mixtures of such compounds with phosphonosuccinic acid or its water soluble salts, often in a minor proportion by weight based on the total weight of the solvent-free mixture.

It is particularly preferred, according to the invention, to use reaction products which comprise: up to 50% by weight of a phosphonosuccinate based on the weight of the solvent-free composition; a phosphonated dimer of maleate; optionally a minor proportion by weight, relative to the weight of dime.r, of higher phosphonated oligomers of maleate; and from 0.5 to 5% by weight of alkali metal phosphate.

According to a further preferred embodiment the invention provides a novel phosphonated oltgomer of a water soluble acrylate comprising an average of from 2 to 15 acrylate units per mole and exhibiting at least one NMR $^{31}$P resonance characteristic of a C—P bond.

According to another embodiment our invention provides a novel vicinel diphosphonate of the formula RCHPO$_3$M$_2$ CHR′PO$_3$H$_2$ where R is a hydroxy, carboxy, phosphono, sulphato and/or sulphono substituted alkyl group having up to 5 carbon atoms, R′ is hydrogen, a carboxylate, a C$_{1-4}$ hydrocarbon or an R group and H is hydrogen or a cation or cattonic group.

The invention further provides the use of the reaction products and novel phosphonated oligomers and vtcinal diphosphonates according to the invention as scale inhibitors or as corrosion inhibitors in aqueous systems, or as detergent builders or chelattng agents for metals.

In particular the invention provides a method for the treatment of potentially scale forming aqueous systems, or of potentially corrosive aqueous systems, to inhibit scaling or corrosion respectively, which comprises adding thereto a threshold amount (e.g. an effective amount less that 100 ppm by wt.) of a novel compound or mixture of compounds according to the invention.

The invention further provides a method for the preparation of a compound or mixture of compounds of the invention, which comprises reacting together water soluble salts of maleic and phosphorous acids in aqueous solution and in the presence of an effective amount of a free radical initiator, and preferably in an aqueous based solvent.

Examples of acetylenically unsaturated compounds which may be used in the method of our invention include propargyl alcohol, propiolates, buta-2,3-yne-1,4-dioates, and other acetylentcally unsaturated alcohols, carboxylate salts and hydroxycarboxylate salts having less than 10 carbon atoms.

The novel vlcinal diphosphono compounds of the present invention may be prepared by reacting an aqueous solution of the acetylenically unsaturated alcohol and/or water soluble salts of the carboxylate reagent, as the case may be, with a phosphite, usually an alkali metal phosphite such as sodium or potassium phosphtte in the presence of free radicals. The free radicals are typically provided by adding sodium persulphate or hydrogen peroxide, in sufficient quantity to convert a substantial proportion, e.g., more than 50%, preferabiy more than 60% of the acetylenlc compound into the diphosphono compound. Instead of water it is possible to use other aqueous based solvents such as aqueous ethanol, aqueous methanol, aqueous dioxan or aqueous acetone. Such solvents are preferred where the acetylenic compound is only sparingly soluble in water.

The reaction may give rise, in addition to the diphosphono derivative, to some phosphonated oltgomers of the acetylenic reagent. These oligomers, and reaction products containing them, have valuable scale and corrosion inhibiting properties and are included in our invention. The reaction may additionally form a proportion (usually minor) of gemtnal diphosphonate. The reaction product also, typically, contains some phosphate. The mixtures of vicine1 diphosphonate, geminal diphosphonate, phosphonated oligomers and/or inorganic phosphate show synergistic activity.

Important differences between the preferred methods of the present invention, and prior art attempts to prepare phosphOnates from olefins using phosphorous acid, include: the use of an aqueous based solvent and the use of salts rather than free acids. The reaction preferably is run at neutral or alkaline pH. Elevated temperatures are preferred and the amount of free radical initiator required is often substantially more than is usually used in free radical catalysed reactions. The initiator is preferably dosed continuously or intermittently to the reaction mixture to the extent required to keep the reaction going to completion.

The method of the Invention preferably employs alkali metal salts of any acid reagents, e.g. an alkali metal proptolate, acrylate, methacrylate and/or maleate and a di-alkaly metal phosphite in each case the alkali metal is preferably sodium, but other cartons which form soluble phosphttes and which do no interfere with the reaction may be used. Examples include calcium, potassium, lithtum and magnesium. Phosphontum (e.g. tetra alkyl or tetrakts hydroxnnethyl), ammonium end substituted ammonium such as tetramethyl ammonium and/or mono-, di- and/or tri- and ethanolammonium may also be used, but are not preferred.

The proportion of phosphite to unsaturated compound is preferably substantially stoichiometric, i.e. equtmolar in the case of ethylenically unsaturated compounds or 2:1 molar in the case of acetylenes. A small excess of either reagent may be present, however substantial excesses of the phosphtte ate generally undesirable. Excesses of the unsaturated compound generally result in the formation of unphosphonated oligomers. Since the latter are usually effective water treatment agents in their own right, and are often useful synergists with the phosphonated products of this invention, comparatively large excesses of the unsaturated agent can be tolerated.

Preferably the mole ratio of ethylentcally unsaturated compound to phosphtte is from 1:5 to 15:1, usually 1:1 to 3:1, especially 1.3:1 to 2.5:1 e.g. 1.5:1. Generally, higher proportions of phosphite to unsaturated compound will be required to phosphonate acetylenes. For instance the proportion of phosphtte to acetylene may be from 10:1 to 1:10, usually 5:1 to 1:8, especially 3:1 to 1:5, e.g. 2.5:1 to preferably 2:1 to 1:1.

The unsaturated compound is preferably a maleate, acrylate or a mixture thereof or a proptolate or allyl or properlyl alcohol. Other olefins and acetylenes include methacrylate, vinyl sulphonates vinyl phosphonates, 2,3-butyne- 1,4-diol, butyne-1,4-dioates, 2,3-butyne-1- ol-4-oates,nor-bornene, vinyl acetate 2,3-butene-1,4-diol and 2,3-butene-1-ol-4oates. Compared with maleares, fumerates have been found comparatively unreactive.

We prefer to carry out the preparations at a concentration of the reagents at which the reaction mixture will just remain fully dissolved and stirrable at the reaction temperature.

The reaction may, however, be carried out in the presence of sufficient solvent to dissolve only part of the reagents, but sufficient, preferably, to form a stirrable slurry. For instance amounts of total solids may be from 0.5 to 96% by weight of the reaction mixture, more usually 1 to 95% e.g. 10 to 90%, especially 20 to 85, preferably 35 to 80%, more preferably 50 to 80%, for example 60 to 78% or 70 to 75%.

The desired concentration may conveniently be achieved by dissolving the reagents in, e.g. water, and evaporating down, e.g. until the mixture is still just stirrable, or by heating a mixture of phosphorous acid and the unsaturated compounds and neutralising with hot concentrated base such as sodium hydroxide, prior to adding the free radical initiator.

The reaction requires a source of free radicals for the system, e.g. an ammonium or alkali metal persulphate or peracetate, hydrogen peroxide, a hydroperoxide, chlorine dioxide, sodium chlorate, sodium hypochlorite, organotin hydrides, azo compounds such as 4,4'-azobiscyanovalertc acid, electrolysis, ultra violet or other ionising radiation or ultrasound, or any combination of the foregoing. With the preferred use of peroxide as a free radical source, phosphonated product yields of 90% have been obtained and the reaction product can be used directly, without purification.

The amount and rate of formation of Free radical generated determines the extent to which the reactton may proceed and the time required.

The amount of free radical initiator used, should be sufficient to take the reaction to completion in reasonable time (e.g. within 0.25 to 24 hours). Smaller amounts may be used tF incomplete reactions can be tolerated. Generally the quantity of free radical required is substantially greater than in normal Free radlcal catalysed reactions. Excess free radical source is, however, preferably avoided on economic grounds and to minimise contamination of the product. Generally the more water present, the more Free radical is required in order to complete the reaction. Also, more elevated temperatures may permtt the reaction to proceed with less addition of free radicals. He therefore prefer to use a concentrated reaction mixture e.g. at least 60% and preferably more than 70% total solids. Under these conditions the amount of initiator requtred Is typically from 1 to 10 mole % e.g. 2 to 8 and preferably from 3 to 6 mole based on the unsaturated reagent. However if the reaction is performed in a more dilute system, and/or at lower temperatures, higher amounts of initiators such as sodium, potassium or ammonium persulphate may be required, typically from 10 to 30 by weight of the unsaturated reagent, e.g. 20 to 25.

The reaction mixture is preferably at a pH at least neutral, or slightly alkaline. Acid pH should be avotded.lypically pH should be above 5 and especially above 5.5 preferably above 6 more preferably above 6.5 e.g. 6.8 to 10 most preferably 7 to 9 at least initially, although the pH may be allowed to drop below 7 as the reaction approaches completion.

The reaction normally precedes in an aqueous based solvent which is typically water, provided the selected reagents are sufficiently soluble. Water mtscible organic solvents may be included, where required for more sparingly soluble reagents. The solvent should contain sufficient water to dissolve the phosphtte to a substantial extent. The organic solvent may for example comprise methanol, ethanol, iso-propanol, ethylene glycol, propylene glycol, a water soluble oligomer of ethylene oP propylene glycol such as diethylene glycol, a water soluble toorio- or di- ether of ethylene or propylene glycol or of an oltgomer thereof, such ethylene glycol monomethyl ether, ethylene glycol dimethyl ether, dethylene glycol monomethyl ether or diethylene glycol mono ethyl ether, glycerol, a water soluble glyceryl ether, acetone, and/or dioxan. The requirement to dissolve the phosphite and the olefin or acetylene in the same aqueous based solvent is the main limitation on choice of unsaturated reagent. Zn cases of difficulty it may be possible to carry out the reaction t n anhydrous d t oxan.

The reaction mixture generally requires heating for at least part of the reaction time in order to initiate and maintain the reaction. Preferably temperatures above 60° C., more preferably above 80° C., e.g. 90° C. to the boiling point of the mixtures are used, and maintained for from 30 mins to 8 hours in order to complete the reaction. Higher temperatures, e.g. under pressure, for example in an autoclave, may be advantageous. Typically the temperature is between 50 and 250° C. e.g. below 200° C. and preferably below 150° C. Optimum temperatures are usually in the range 95°–140° C. e.g. 100°–130° C.

We prefer that the reaction should be carried out under an inert atmosphere, e.g. nitrogen. This helps to improve the yield of product.

The reaction may be carried out batchwise, semi-continuously or continuously e.g., in a pipe reactor. The free radical source may all be added Initially or, preferably, in a plurality of additions, or continuously or semi-continuously throughout the reaction.

To maximise the yield of phosphonated product tt is sometimes necessary to add the unsaturated reagent, continuously or intermittently during the reaction period to an aqueous solution of the phosphite.

The product typically contains a proportion, e.g. in the case of maleares, up to about 40%, by weight thereof, of the phosphonate monomer (e.g. phosphonosuccinate) the remainder comprising a phosphonated dimer posstbly wtth small amounts of higher homologues, and inorganic salts such as phosphates.

In the most preferred method of preparing a water soluble organic phosphonate by reacting a water soluble olefinic or acetylenic carboxylate salt or alcohol with a water soluble phosphite salt in the presence of water, the quantity of water used is less than about 50% by weight which is generally less than that required fully to dissolve the reagents at room temperature, the temperature is sufficiently elevated to provide a stirrable reaction mixture and hydrogen peroxide (or other peroxide source) is used and is present in an amount effective to maintain the reaction.

As noted, other peroxides than hydrogen peroxide can be used, also free radical sources generally can be used.

In this preferred embodiment, the amount of water present initially, is preferably less than 40% by weight based on the total weight of the reaction mixture, e.g., less than 35% especially less than 32%. Generally we prefer that the amount of water be greater than 10%, preferably greater than 15% e.g., greater than 20%, most preferably more than 25% by weight based on the total weight of the reaction mixture. Thus, water is preferably used in an amount of 10% to 40% by weight and most preferably 25-32% by weight.

The proportion of peroxide is typically an effective amount up to 25% molar, based on the unsaturated compound. We prefer to use only sufficient peroxide to initiate the reaction to a substantial extent, e.g. to provide yields of phosphonated product greater than 70% molar based on the unsaturated compound preferably greater than 80% molar, e.g. greater than 85% molar. This minimum amount of peroxide depends on the amount of water and is generally reduced as the amount of water is reduced. For example at 30% wt/wt water, yields of about 90% can be obtained using between 4 and 6 mole % of peroxide based on the unsaturated compound.

The temperature of the reaction is preferably above 60° C. more preferably above 70° C., typically at the boiling point of the mixture. Rapid refluxing and agitation favour the reaction, and we therefore prefer to carry out the process under conditions which promote rapid evaporation such as a wiped film or spray evaporator, preferably incorporated in a loop reactor.

Thus the reaction mixture may be continuously recycled through an evaporator and reagents and initiator continuously or intermittently added.

The ratio of unsaturated compound to phosphite typically determines the proportion and mean degree of polymerisation of any dimer or higher polymers formed. We prefer to use molar ratios greater than 1 but preferably less than 2, e.g. 1.2 to 1.5, e.g. 1.3

We have found high pH an advantage. Generally the pH should be above 5, suitably above 7, preferably above 7.5, more preferably above 8, especially above 8.5 to 9.5, e.g. 9 to 10. Although even higher pH's can be used, at a pH much above 10 (e.g. a pH of 12) the corrosiveness of the solution that results reduces the practicality of using such a high pH especially if direct use of the reaction mixture is contemplated.

If it is desired to purify the product, e.g., by separating phosphonated monomer from the phosphonated oligomers, it is possible to esterify the products to form, e.g., methyl esters and distill off the phosphonated monomer. However, an advantage of the present method is that expensive purification of the reaction product is generally not necessary. The mixture is an effective water treatment agent in its own right, and its efficiency is enhanced by synergism.

We believe that one reason for the high useful purity yields available with this most preferred method wherein peroxide is the free radical source, is based in the low reactivity of the transisomer of the olefin being chemically activated, e.g. by carboxylate and/or hydroxyl groups. More specifically, as shown in Example 22 below, a high yield, high purity product is formed when the olefin is a maleate (cis isomer) and hydrogen peroxide is used as the free radical source. Similar results are not possible with fumarate (trans isomer). In fact, we have found that trans isomers tested have low activity especially when the source of free radicals is persulfate. With peroxide as a source of free radicals, we have been able to achieve a yield of only about 30% with fumarate (trans isomer) and the proportion of monomer to dimer and other higher molecular weight material appears to be much larger than in the case of maleates (cis isomer).

The unexpectedly good results obtained using the peroxide free radical source as compared with persulfate, appears to be partly due to the isomerization of part of the maleate to fumarate when persulfate is used and the lack of such isomerization with peroxide. As noted above, fumarates have very little if any reaction with persulfates leaving fumarates as unreacted impurities in the reaction mixture along with sulphate residues.

The phosphonation reaction product of maleate salts using peroxide contains a mixture of salts of phosphonated dimer of maleic acid (1-phosphono-1,2,3,4-tetracarboxybutane) and phosphonosuccinate in sufficiently pure form that it can be used directly, without further purification.

In view of the fact that phosphonosuccinic acid and its salts are relatively poor scale and corrosion inhibitors, we attribute the strikingly enhanced performance of our novel reaction products, or at least those derived frOM maleares, to the presence either of higher homologues or of chemically modified oligomers, e.g. hydroxyl or sulphate derivatives and/or to the presence of inorganic phosphate. We believe that certain of these homologues may be inherently superior to phosphonosuccinates as scale and corrosion inhibitors. We also believe that there is synergistic action between the components of our novel reaction products.

We have found that a synergism is shown with a mixture of phosphonosuccinic acid and the novel phosphonate dimer of maleic acid produced by the phosphonation of maleic acid using the peroxide free radical source. The synergism is shown for substantially all mixtures although particularly marked synergism is shown for mixtures containing the phosphonate dimer of maleic acid in amounts of 8% to 65% by weight based on total weight of the mixture of phosphonosuccinate and dimer. Particularly preferred is a mixture containing from 10% to 60% by weight of the dimer based on the mixture weight, and more especially 12-50%. The reaction product contains about two-thirds phosphonosuccinate and one-third of the dimer, which is in the middle of the range for particularly marked synergism.

There is evidence that some higher oligomers are also present which can be represented as $H_2PO_3[C(COOH)—C(COOH)_mH$ where m is an integer or $H_2PO_3[C(COOH)_nH$ where n is an even numbered integer (e.g. 1-phosphono-1,2,3,4,5,6-hexacarboxyhexane). However, these are present in relatively small quantities which do not require removal for use of the reaction product.

The compounds oP mixtures of our invention are or particular value as corrosion inhibitors in systems containing calcium ions and may also be used in conjunctton with zinc salts.

The products are effective in the presence of chlorine, chlorine dioxide, bromine, hypochlortte, hypobromite and other oxtdislng biocides. They Hay therefore be used to treat chlorinated Nater systems or systems stertltsed by other oxidising agents. They are useful in cooling water treatment, treatment of industrial process water, boiler water treatment, desalination plant and For treating water used or produced in otl wells including injection water, produced water, and water used for hydrostatic testing of pipelines.

They are also of value as detergent butlders or auxiliary builders, e.g. in conjunction with zeolites, or as metal chelattng agents, e.g. in metal extractions. They may be used in aqueous based functional fluids such as hydraulic fluids, lubricants, curttrig fluids and otl field drilling muds.

For example the compounds and mixtures of the invention may be used in squeeze treatment of oll wells in conjunction with calcium salts, or may be added to drilltng muds or to oilfield injection water, produced water or water for hydrostatic testing, as well as to various industrial cooling waters and process waters and to water for use in central heating systems. They are especially effective in preventing barium sulphate scale.

Squeeze treatment of boreholes, e.g. to prevent formation of $BaSO_4$ scale, typically entails impregnating the formation in the environs of the hole with a calcium salt of the inhibitor, which is subsequently leached into any aqueous system circulating in the hole to provide controlled slow release.

For example in oil wells the hole is flushed out with aqueous surfactant to provide a water wettable surface and then impregnated with a solution of the inhibitor. The calcium salt is formed in situ either by calcium in the formation, where the latter comprises limestone, or by subsequent treatment of the hole with an aqueous calcium salt, e.g. where the formation comprises sandstone.

The compounds and mixtures are useful in treating chlorineted water systems for which many threshold agents are ineffective. Effective concentrations may typically range from 0.1 to 50 ppm depending on the nature of the aqueous system preferably 0.5 to 20 ppm especially to 10 ppm e.g. 1.5 to 4 ppm.

Products according to the invention may be used in combination with one another, and/or tn conjunction with other water treatment agents including: surfactants, such as arttonic surfactants (e.g. $C_{10-20}$ alkyl benzene sulphonates, $C_{10-20}$ olefin sulphonates, $C_{10-20}$ alkyl sulphates, $C_{10-20}$ alkyl 1 to 25 mole ether sulphaies, $C_{10-20}$ parafin sulphonates, $C_{10-20}$ soaps $C_{10-20}$ alkyl phenol sulphates, sulphosucctnates, sulphosuccinamates, lignin sulphonates, fatty ester sulphonates, $C_{10-20}$ alkyl phenyl ether sulphates, $C_{10-20}$ alkyl ethanolamide sulphates, $C_{10-20}$ alpha sulpho fatty actd salts, $C_{10-20}$ acyl sarcoslnates, isethionates, $C_{10-20}$ acyl taurides, $C_{10-20}$ alkyl hydrogen phosphates), non-tonic surfacianis (e.g. ethoxylated and/or propoxylated $C_{10-20}$ alcohols, ethoxylated and/or propoxylated $C_{10-20}$ carboxylic actds, alkanolamdes, amine oxtdes, and/or $C_{10-20}$ acyl sorbltan and/or glceryl ethoxylates) amphoteric surfactants (e.g. betathee, sulphobetatnes, and/or quaterised imidazolines), and/or cationic surfactants (e.g. benzalkontum alts, $C_{10-20}$ alkyl trimethyl ammonium salle, and/or $C_{10-20}$ alkyl trimethyl or tris(hydroxymethyl) phosphonum salts); sequestiants, chelattng agents, corrosion Inhibitors and/or other threshold agents (e.g. sodium tripolyphosphate, sodlum ethylenedfamine terracetare, sodium nitrilo triacetate, tetra potassium pyrophosphate, acetodiphosphonlc acid and its salts, ammonium trsmethylene phosphontc acid and its salts, ethylenediamlne teirakls (methylene phosphonic) actd and its salts, diethylenetrtamne pentaRts (methylene phosphonic) acid and its salts); tolyltriazole and mixtures of ntirte, benzoate, HHP and/or PTCB) biocides (e.g. tetrakis (hydroxymethyl) phosphontum salts, formaldehyde, glutaraldehyde); oxidising bioctdes and/or bleaches (e.g. chlorine, chlorine dioxide, hydrogen peroxide, sodium perborate); foam controlling agents such as silicone antifoams; oxygen scavengers such as hydrazines and/or hydroxylamnes; pH controlling and/or buffering agents suc as amines, borates, citrates and/or acetates; chromium salts; zinc salts; and/or other water treatment agents such as polymeric dispersants and coagulants (ncluding polymaleic, polyacryltc and polyvtnylsulphonic acids and their salts, starches and/or carbox methyl cellulose, and/or molybdates. The Invention provides formulations comprising an effective amount of a product of the invention as aforesaid and any of the aforesaid known water treatment agents. Such formulations may, for example, contain from 5 to 95% by weight of a product of the invention and from 5 to 90 by wetght of one or more of any of the aforesaid water treatment agents.

Detergents ccording to this invention may comprise 2 to 70% preferably 3 to 50 e.g. 5 to 20% by weight surhctant and 5 to 60%, preferably 10 to 45% e.g. 15 to 30% by weight total builder, the major portion of any balance being typically a carrier, solvent or diluent.

The builder may consist of a phosphono or diphosphono product according to this Invention. Alternatively the builder may comprise such a product together with one or more other builders such as zeoltte, sodium tripholyphophate, potassium pyrophosphate sodium or potassium carbonate, sodium citrate, sodium nitrilotriacetate, sodium silicate and or sodium ethylene diamine terracetare. Thus the product of the invention may consitute from 1% to 100% of the total builder, e.g. 5 to 90% especially 10 to 80%. The balance may comprise an inert solid such as sodium sulphate, or a liquid medium such as water or a low molecular weight polethlene glycol. The detergent may additionally comprise: up to 5% by weight, e.g. 0.01 to 2% by weight, of optical brightener; up to 5% by weight e.g. 0.01 to 2% by weight of soil suspending agent such as sodium carboxymethyl cellulose; and up to 6%, more usually up to 2%, by eight, each, of perfume, dye enzyme, bleach, buffers and of the conventional ingredients of solid or liquid detergent composition.

The invention will be illustrated by the following examples. All preparations were carried out under an atmosphere of nitrogen.

The evaluations were performed in accordance with the following test methods:

Test Method No. 1

Synthetic seawater brine having total $CO_2$ content of 100 $mg.l^{-1}$ is prepared to the following formulation:

| | Formulation |
|---|---|
| Component | Concn. $(g.l^{-1})$ |
| NaCl | 49.06 |
| $MgCl_2.6H_2O$ | 22.21 |
| $Na_2SO_4$ | 8.18 |
| $CaCl_2.2H_2O$ | 3.074 |
| KCl | 1.390 |
| KBr | 0.202 |
| $NaHCO_3$ | 0.191 |
| pH | 8 |

500 ml of synthetic seawater concentrate and the appropriate amount of a 0.5 gm/litre stock 'solution of the inhibttor are heated to, and maintained at, 80° C. and pH adjusted to 8.00+0.01. 0.125 gm of precipitated calcium carbonate, having 60% by weight aragonite and 40% calcite, is added and the pH monitored for 60 minutes.

If no drop in pH greater than 0.1 units is observed the inhibitor is providing 100% inhibition of aragonite scaling. The test is repeated until the minimum (threshold) concentration for 100% inhibition has been determined.

Test Method No. 2

Synthetic formation water is prepared, having the Formula:

| | |
|---|---|
| NaCl | 110.08 g |
| $Na_2SO_4$ | 16.265 g |
| $NaHCO_3$ | 5.25 g |
| $MgCl_26H_2O$ | 35.55 g |
| $CaCl_2H_2O$ | 9.535 g |
| $SrCl_26H_2O$ | 0.26 g |
| KCl | 2.955 g |
| $H_3BO_3$ | 0.43 g |
| pH | 7.8 |

The synthetic formation water is seeded with precipitated calcium carbonate and pumped through a 1/6 inch bore capillary tube at 90° C. and at a rate of 25 ml/min until the pressure across the tube reached 5 psi, The inhibitor is observed to determine any continuing rise. The minimum concentration of inhibitor to stop further rise of pressure is determined, Test Method Nos. 3 and 4

These tests are based on the measurement of linear polarisation using an "ELECTROCHEHICAL INTERROGATOR" to determine the corrosion current, The rate of corrosion is expressed in mm per year of iron lost from the surface of the carbon steel work electrode. The auxiliary electrode is platinium and the reference electrode satur&ted calomel, The calcium test (Method 3) used medium containing 120 ppm Ca++ and 213 ppm Cl− at a pH of 7.5 and a temperature of 25° C.

The zinc test (Method 4) used a medium containing 20 ppm Zn++, 200 ppm Cl−, a pH of 7.5 and a temperature of 25° C.

Both tests used 60 ppm inhibitor (expressed as the acid) and swept from −20 mv to +20 mv with respect to rest potential in minute.

Example 1

A solution of maleic actd (1.74 Kg, 15M) and sodium hydroxide (1.2 Kg, 30N) in water (4.5 L) was added over 1 hr 40 min to a stirred refluxing soluiion (102°–103° C.) of $H_3PO_3$(820 g, 10M) and sodium hydroxide (800 g, 20M) in water (2 L). Over this period a solution of ammonium persulphate [684 g, 20 mol % (w.r.t. maleic acid)] in water (1.3 L) was added dropwise. After these additions the reaction mixture was refluxed for 15 mins and then a further 5 mol ammonium persulphate solution (171 g 330 ml water) was added dropwise over 30 min. After a further 30 min reflux the solution was allowed to cool slowly. A $^{31}P$ n.m.r. spectrum of thls reactton mixture ($D_2O$) showed that 88% of the phosphorous acid had reacted and that 5% had been oxidised to $H_3PO_4$. 40% by wt. of the organo-phosphonic acids present was phosphonosucctnic acid (n=1) and 60% by wt. higher homologues with n>1. A $^1H$. n.m. spectrum indicated that approximately 85% of the disodium maleate had reacted. The average value of n is therefore approximately 1.5. The product contains about 2% by weight of sodium phosphate.

Example 2

A solution of maleic acid (174 g, 1.5M) and sodium hydroxide (120 g, 3H) in water (450 ml) was added dropwise over 1 hr 20 min to a stirred refluxtng solution of $H_3PO_3$(82 G, 1M) and sodium hydroxide (80 g, 2 H) in water (200 ml). During this period sodium persulphate (71.4 g, 20 mol % w.r.t. maleic acid) was added in porttons- to the teaetlon mtxture. After these additions the solution was refluxed for 15 minutes and then another 5 mol % of sodium persulphate (17.9 g) was added over 30 mins. The solution obtained was refluxed for a further 30 mins and then allowed to cool to room temperature. $^{31}P$ and $^1H$ n.m.r. spectroscopy indicated a product. identical to the first example.

Example 3

A solutton of acrylic acid (72 g, $^1H$) and sodium hydroxide (40 g, 1M) in water (200 ml) was added dropwise over 0.75 h to a stirred refluxing solution of phosphorous acid (8.2 g, 0.1M) and sodium hydroxide (8 g, 0.2M) in water (100 ml). During this time sodium persulphate (47.6 g, 20 mol % wrt to the acrylic acid) was added portionwise. The solution obtained was boiled for 0.25 h and then sodium persulphate (10 g) was added over 0.25 h to this boiling solution. $^{31}P$ n.m.r. spectral data indicated that 30 mol % of the phosphorous acid had been oxidieed to phosphate; the remainder had reacted with the acrylic acid to produce a phosphonate matarial. A $^{13}C$ n.m.r. spectrum indicated that all the acrylate had reacted. The product must therefore contain ca. 14 acrylic acid units to each phosphorus.

Example 4

A solution of acrylic acid (9 g, 0.125M), maleic acid (14.5 g, 0.125M) and sodium hydroxide (15 g, 0.375M) in water (250 ml) was added dropwise over one hour to a stirred refluxing solution of phosphorous acid (10.3 g, 0.125M) and sodium hydroxide (10 g, 0.25M) in water (100 ml). During this pertod sodium persulphate (11.9 g, 20 mol % wrt olefins) was added portionwise. The solution obtained wa refluxed for 0.25 hr and then allowed to cool to room temperature. A $^{31}P$ n.m.r. spectrum indicated that 67 mol % of the $H_3PO_3$ had reacted to give material containing PC bonds and 13 mol %% had been oxtdsed to phosphate. $^{13}C$ and $^1H$ n,m,r. spectral data indicated that all the acrylic acid and ca, 90% of the maleic acid had reacted. Therefore the material formed has 1.5 acrylic acid and 1.3 maleic acid units to each phosphorus.

Example 5

The product of Example 1 was tested for scale inhibition in comparison with sodium phosphonosucctnate and PTCB using the aragonite test (Test Method No 1 above). The test results are listed in Table 1, expressed as ppm of the 100% inhibitor. The test was repeated in the presence of 3 ppm chlorine and again after the product had been exposed to 3 ppm chlorine dioxtde for 1 hour at 60° C. with identical results.

The results of a test of tube blocking with aragonite scale (Test Method No 2 above) are also recorded n Table 1.

The product was steam distilled and no phosphorus was detected in the distillate.

TABLE 1

| Test | Example 1 | Phosphonosuccinate | PTCB |
|---|---|---|---|
| Aragonite (Test No 1) | 1.4–1.5 | 4.7–4.8 | 1.0–1.1 |
| Tube Blocking (Test No 2) | 0.5–0.6 | 1.0–1.4 | 0.8–1.0 |

Example 6

Vinyl sulphontc acid (100g of a 30/w iolution of the sodium salt, 0.23M) was added dropwise over 0.25 h to a refluxing stirred solution of phosphorous acid (6.28 g, 0.07M) and sodium hydroxide (6.12 g, 0.15H) in water (100 ml). During this period sodium persulphate (10.9 g, 20 mol % w.r.t. vinyl sulphontc acid) was added portionwise. The reaction mixture was boiled for a further 0.5 h. $^{31}$P n.m.r. analysis of the reaction mixture Indicated that 82 mol % of the phosphorous acid had reacted to give organo-phosphorus materials. All the remaining phosphorous acid had been oxidieed to phosphate. $^{13}$C n.m.r. data indicated that all the vinyl sulphonic acid had reacted and therefore that the product contained on average 3.7 vinyl sulphonlc acid groups to each phosphorus.

Example 7

A solution of allyl alcohol (58 g, 1M) in water (500 ml) was added dropwise over 5 h 10 min to a stirred refluxing solution of phosphorous acid (82 g, $^1$H) and sodium hydroxide (80 g, 2M) in water (200 ml). During this period sodium persulphate (59.5 g, 25 mol % w.r.t. the allyl alcohol) was added porttonwlse. The product obtained as analysed by $^{31}$P and $^{13}$C n.m.r. spectrscopy. This indicated that ca. 71 mol % of the phosphorous acid had reacted and ca. 14 mol % had been oxidieed to phosphate. All the allyl alcohol had reacted, therefore the product obtained contains an average of 1.4 allyl alcohol units to each phosphorus.

Example 8

A solution of vinyl phosphonic acid (19.3 g 0.1M) and sodium hydroxide (14.3 g, 0.36M) in water (200 ml) was added dropwise over 2.75 h to a stirred refluxing solution of phosphorous acid (5.1 g, 0.062M) and sodium hydroxide (4.93 gm. 0.123 m) in water (100 ml). A solution of sodium persulphate (8.8 g,.ca.20 mol % w.r.t. the vtnyl phosphontc acid) in water (65 ml) was added simultaneously over the same period. After these additions the reaction mixture was boiled for ca. 1.5 h and then a solution of sodium persulphate (4 g) in water (25 ml) was added dropwise over 0.5 h. $^{31}$P n.m.r spectroscopy of the reaction mixture indicated that all the vinyl phosphonic acid had polymerised and that ca. 25–30% of the phosphorous acid had been incorporated into the product polymeric mixture. The remaining unreacted phosphorous add had been oxtdised to phosphate.

Example 9

A solution oF maleic acid (116 g, 1M), sodium hydroxide (106 g, 2.65 m) and phosphorous acid (12.5 g, 0.15M) in water (450 ml) was heated to 95° C. in a hotling Hater bath. Sodium persulphate (60 g, 0.25M) was added In small portions at 5 minuLe Intervals to the well stirred solution over a period of eight hours. A further portion of sodium hydroxide (5.5 g) was added after 5 hours to keep the solution alkaline and prevent rapid oxygen evolution when the persulphate was added. Analysis of the product as in Example One showed that 17% of the phosphorous acid used had been convered to phosphate 9% remained unreacted, 26% had been converted to phosphonosuccinic acid and the remainder to polymeric species. The average n was 5.2.

Example 10

A solution of maleic acid (110 Kg, 950M) and sodium hydroxide (170 Kg of a 47% aqueous solution 2000M) on water (255 Kg) was added slowly over 3 h to a stirred refluxing solution of phosphorous acid (60 Kg, 732M) and sodium hydroxide (125 Kg of a 47% solution, 147M) tn water (90 Kg). 100L of a solution of sodium persulphate (67.9 Kg, 285M(30 mol % w.r.t, maleate)) in water (116 Kg) (150 L in total) was added simultaneously over the same pertod. The reactlon mixture was refluxed for 1 h after which the remaqning sodium persulphate solution (50 L) was added over 0.5 h. Refluxing was continued for a further 3 h after which the reaction was allowed to cool. Analysis of the product indicated a very similar composition to that described in Example One, ca. 84 mol % of the phosphorus acid had reacted and 12 mol % had been oxtdised to phosphate.

Example 11

The product of Example 1 was tested against sodium phosphonosucclnate, a mixture of equal parts by weight sodium phosphosuccinate and sodium polymaleate, PTCB and HPP In corrosion inhibition tests "calcium only" (Test Method No 3 above) and "zinc only" (Test Hethod No 4 above). The results in mm/yr are recorded in Table 2.

TABLE 2

| Inhibitor | Ca++ 3.5 hrs | Ca++ 20 hrs | Zn++ 3.5 hrs | Zn++ 20 hrs |
|---|---|---|---|---|
| Blank | 0.270 | — | — | — |
| Sodium Phosphonosuccinate | 0.135 | — | — | — |
| Sodium Phosphonosuccinate and Sodium polymaleate | 0.069 | 0.068 | — | — |
| Example 1 | 0.048 | 0.020 | 0.021 | 0.020 |
| PTCB | 0.064 | 0.079 | — | — |
| HPP | 0.025 | 0.008 | 0.246 | 0.160 |

Example 12

The product of examples 1, 3 and 4 were compared using test methods 1, 2 and 3(above). The results are reported in the following Table 3.

TABLE 3

| Inhibitor | Example 1 | Example 3 | Example 4 |
|---|---|---|---|
| Test No. 1 | 2.3 | 5–10 | 2.7–2.9 |
| Test No. 2 | 1.4 | 2.4–2.8 | 1.0–1.2 |
| Test No. 3 | | | |
| (i) after 3½ hours | 0.048 | 0.037 | 0.029 |
| (ii) after 20 hours | 0.02 | 0.03 | 0.021 |

Example 13

The product of Example 1 was found to give 100%, inhibition of barium sulphate scale after 4 hours at a level of 50 ppm. in water at 90° C. containing 126 mg $l^{-1}$ barium ion and 1210 mg $l^{-1}$ sulphate ion at pH 6.5 (determined at 25° C.). The inhibition after 24 hours was 82%.

Example 14

A solution of propargyl alcohol (28 g, 0.5M), made up to 500 ml with water was added dropwise over 6 h to a stirred refluxing solution of phosphorous acid (82 g, 1.0M) and sodium hydroxide (80 gm 2.0M) in water (200 ml). The reaction was maintained under an atmosphere of nitrogen. During the addition period sodium persulphate (ca. 48 g) was added portionWise (about 8 g $h^{-1}$). A further 10 g of sodium persulphate was then added over about 0.5 h. Water (ca 500 ml) was added and about 500 ml was distilled from the reaction mixture to remove any propargyl alcohol as an azeotrope with water, lhe dark brown solution obtained was analysed by $^{31}P$ n.m.r. spectroscopy (in $D_2O$). The reaction consists of ca. 70 mol %; organo-phosphorus compounds; the majority of which (ca. 80% ) is 1,2-diphosphono 3-hydroxy-propane. The remaining 30 mol % of phosphorus was ca. half oxidised to phosphate and half remained as unreacted phosphorous acid. $^{13}C$ n.m.r. data was consistent with the product outlined above.

Example 15

The product or example 14 was taken without purification and tested for scale and corrosion inhibition as follows:

(a) Scaling (Test Method 1)

The product of Example 14 provided 100% inhibition of aragonite scale at a concentration of 1.0–1.2 mg. $1^{-1}$ total active expressed as phosphonic acid.

This is sufficient to indicate commercial utility as a scale inhibitor.

(b) Corrosion Inhibitor (Test Method No. 3)

After a contact time of 3.5 hours the corrosion rate was measured at 0.043 mm/yr. After 20 hours the corrosion rate was measured as 0.029 mm/yr. This indicates potential commercial utility as corrosion inhibitor.

Corrosion inhb(tion has been observed at concentrations below 10 ppm, which correspond to the levels of HPP required. The novel compounds or the invention moreover retain their activitly tn chlorinated water systems, systems, unlike HPP.

Example 16

In a field test, an open recirculating cooling water system in a chemical manufacturing plant was operating under the following conditions;

| | |
|---|---|
| rate of circulation | 120 m$^3$/hr |
| cooling tower inlet temp. | 33° C. |
| cooling tower outlet temp. | 25° C. (at 18.3° C. wet bulb) |
| heat load | 4 × 10$^6$ KJ/hr |
| make up water | 3600 kg/hr |
| blowdown | 2300 kg/hr |
| acid dose rate (36% HCl) | 0.313 Kg/hr |
| product of Example 1 (dose rate) | 0.72 Kg/hr |
| pH of Cooling water | 6.8 |
| conductivity | 1050 microsiemens |
| product of Example 1 (concentrations) | 55 mg l$^{-1}$ |
| calcium hardness | 260 mg l$^{-1}$ |
| total hardness | 340 mg l$^{-1}$ |
| chloride | 260 mg l$^{-1}$ |
| tolyltriazole (copper corrosion inhibitor | 1.0 mg l$^{-1}$ |

A continuous corrosion probe gave measurements of the corrosion between 0.025 and 0.076 mm per year. Coupons of mild steel and copper were suspended in the cooling water. After 25 days the coupons were retrieved and weighed. The steel coupon was found to have lost metal at a rate equivalent to 0.034 mm/year. The copper coupon lost metal at a rate equivalent to $7.6 \times 10^{-4}$ mm/yr.

The foregoing corrosion rate qualtfles as "excellent" protection according the standard defined in "Cooling Water Treatment—a Code of Practice," P62, Appendix A4, Section L, published in 1982 by the Industrial Water Society,

Example 17

A solution of methacrylic acid (43 g, 0.5M) and sodium hydroxide (20 g, 0.5M) in water (300 ml) was added dropwise over 3 h to a stirred refluxing solution of phosphorous acid (13.7 g, and sodium hydroxide (13.4 g, 0.33M) in water (100 ml). Sodium persulphate (23.8 g, 20 mol % w.r.t. the methacrylic acid) was added portionwise over this period. After this a further 0.5M of methacrylic acid and 20 mol % of sodium persulphate were added in a like manner. A $^{31}P$ n.m.r. spectrum indicated that ca. 61% of the phosphorous acid had reacted to give organophosphorus materials. $^{13}C$ n.m.r. indicated that all the methacrylic acid had reacted and therefore that the resulting product contains on average 10 methacrylate units to each phorphorus.

Example 18

A solution of butyn-1,4-diol(10.8 g, 0.125M) in water (200 ml) was added dropwise over 5 h to a stirred refluxing solution of phosphorous acid (20.55 g, 0.25M) and sodium hydroxide (20 g, in water (100 ml). Over this period a solution of sodium persulphate (11.9 g) in water (130 ml) was added simulataneously. A $^{31}P$ n.m.r spectrum of this reaction mixture indicated that ca. 11% of the phosphorous acid had been converted to organophosphorus compounds.

Example 19

A solution of acetylene dicarboxylic acid (mono potassium salt) (50 g, 0.329M) and sodium hydroxide (13.2 g, 0.329M) in water (150 ml) was added dropwise over 5 h to a stirred refluxing solution of phosphorous acid (53.9 g, 0.658M) and sodium hydroxide (52.6 g, 1.316M) in water (200 ml). Over a period of 6 h (starting at the same time as the acetylene dicarboxylic acid addition) a solution of sodium persulphate (31.3 g) in water (130 ml) was also added.

A $^{31}P$ n.m.r. spectrum of the reaction mixture indicated that ca. 30 mol % of the phosphorous acid had reacted to give organophosphorus compounds.

Example 20

A solution of acetylene carboxylic acid (10.1 g, 0.144M) and sodium hydroxide (5.8 g, 0.144M) in water (200 ml) was added dropwise over 5.5 h to a stirred refluxlng solution of phosphorus acid (23.66 g, 0.288M) and sodium hydroxide (23.0 g, 0.575M) in water (150 ml). A solution of sodium persulphate (13.7 g) in water (130 ml) was also added simultaneously over this period. The reaction mixture obtained was studied by $^{31}P$ and $^{13}C$ n.m.r. spectroscopy. This indicated that ca. 85 mol % of the phosphorous acid had reacted to give organophosphorus compounds and 12 mol % had been oxtdised to phosphate. The main organophosphorus component (which contained ca. 50 mol % of the reacted phosphorus) was 2,3-diphosphonopropanotc acid. No acetylene carboxyltc acid remained unreacted.

Example 21

A solution of maleic acid (58 g, 0.5M), phosphorous acid (41 g, 0.5M), and sodium hydroxide (80 g 2M) in water (300 ml) was evaporated in vacuo until a ca. 75% w/w solids/25% w/w water mixture was obtained. This mixture was heated (temperature maintained between 110 and 120° C.) and stirred under an atmosphere of nitrogen. Over a period of 1 h a solution of sodium persulphate (6 g), 5 mol % w.r.t. the maleate) in water (50 ml) was added dropwise. ca. 10 g of water was also distilled out of the reaction mixture during this period. After the addition the reaction mixture was allowed to coal to give a viscous clear otl. $^{31}$P n.m.r. Spectroscopic analysis indicated that 82% of the phosphtte had reacted to give organophosphorus material.

Example 22

A solution of maleic acid (116 g, 1.0M), phosphorous acid (63.1 g 0.77M) and sodium hydroxide (301 g of a 47% w/w solution) in water (230 ml) was heated to reflux and water distilled from the reaction mixture until a mixture that contained 30% water was obtained. Hydrogen peroxide (19.4 g of a 35% solution) was added then dropwise over 1 hour to the stirred refluxing mixture. An exothermic reaction was observed after which the reaction mixture was diluted with water to obtain a ca.5% solution. $^{31}$P n.m.r. spectroscopy of the reaction mixture indicated that ca. 96 mol % of the phosphorous acid had reacted to give organophosphorus materials. $^{13}$C n.m.r. data indicated that >95% of the maleic acid has reacted.

The product was analyzed by ion chromatography using a "DIONEX" (Registered Trade Mark) 4401 ion chromatograph equipped with a gradient pump, conductivity detector of sensitivity 30 us, UV detector (wavelength 215 mm, sensitivity 1.0 aufs) anion membrane suppressor and column oven, with AS5a analytical column and AG5a guard column, employing the following concentration gradient:

|  | % H$_2$O | % 400 mM Na OH |
| --- | --- | --- |
| Initial | 95 | 5 |
| 20 mins | 50 | 50 |
| 30 mins | 50 | 50 |

The run time was 30 mins. at a flow rate of 1.0 ml/min, regenerant flow 4.0 ml/min, column temperature 40° C. and sample concentration 50 mg in 50 ml H$_2$O.

The analysis showed peaks inter alia at 8.82 mins, 12.65 mins, 16.65 mins, 17.68 mins, and 18.77 mins (see FIG. 1). The peak at 8.82 mins has been positively identified as due to phosphate and that at 12.65 mins as phosphonosuccinate. The peaks at 16.65, 17.68 and 18.77 are attributed to different diastereomers of the phosphonated dimer.

(i) Separation of high molecular weight material from Example 22

A sample of the material described in Example 22 was converted to the free acid by precipitation/filtration of sodium chloride with excess conc. HCl and methanol. After removal of the excess HCl by evaporation, an aqueous solution of the remaining material was stirred with an ion exchange resin (Amberlite resin IR—120(H) 0.3-1.18 mm) to remove as much residual sodium as possible. This material was freeze dried and then boiled with a large excess of trimethylorthoformate until no further methylation was observed (by phosphorus n.m.r.). Evaporation of the excess trimethylorthoformate yielded a dark brown oil which was high vacuum distilled (max. head temp. was 155 degrees at ca. 3 mmHg). This yielded 42.2 g of distilled material (phosphorus n.m.r. spectroscopy indicated that this material was tetramethylphosphonosuccinate with a small amount of trimethylphosphate) from 67.7 g of methylated material. The undistilled dark brown/black residue was added to conc. HCl and boiled for 5 hours. Treatment with activated charcoal, filtration and then evaporation of the filtrate yielded 10.7 g of a solid yellow material.

Example 23

Sodium hydroxide (262.1 g of a 47% w/w solution, 3.08M) was added dropwise to a solution of phosphorous acid (116.3 g, 1.54M) in water (415 ml). After this addition maleic anhydride (196 g, 2.0M) was added slowly over 0.5 hours then a further 340.4 g of sodium hydroxide (47% w/w, 4M) was added dropwise followed by a further 15 ml of water. The reaction mixture was adjusted to ca. pH 9 with sodium hydroxide and then water (600 g) was distilled from the mixture to obtain a ca. 68% solids solution. Hydrogen peroxide (9.7 g of a 35% solution) was then added over 1.5 hours to the stirred refluxing reaction mixture. The mixture was further refluxed for 0.25 hours and then, after cooling, water (ca. 270 ml) was added to obtain a ca. 50% solution. Phosphorus n.m.r. spectroscopy indicated that ca. 95 mol % of the phosphorous acid had reacted to give organophosphorus material and the remainder had been oxidized to phosphate.

Example 24

Prepared Using a 50% Heel

A solution of maleic acid (58 g, 0.5M), phosphorous acid (31.6 g, 0.39M), sodium hydroxide (150.2 g of a 47% solution), 257 g of a 50% solution of Example One (adjusted to pH 9.0 and ca. 92% pure by phosphorus n.m.r. spectroscopy) and water (115 ml) was heated to reflux and 245 g of water distilled out to obtain a ca. 70% solids solution. To this stirred refluxing mixture hydrogen peroxide (5-6 mol % w.r.t. maleate) was added over 20 mins. The reaction mixture was then cooled. Phosphorus n.m.r. spectroscopy indicated a total yield of 94% of organophosphorus material.

Example 25

Prepared Via a Semicontinuous Method 184 g of a 70% solution of the material prepared in Example 22 was heated to reflux. Over a period of 1 hour 40 min. a solution of maleic acid (58 g, 0.5N), phosphorous acid (31.6 g, 0.39M), sodium hydroxide (150.5 g of a 47% solution) in water (115 ml) was added dropwise. Simultaneously, hydrogen peroxide (4.8 g of a 35% solution) was added and water (177 g) was distilled out over the addition period. After the additions a further 1.5 g of hydrogen peroxide was added dropwise over 20 mins to the refluxing reaction mixture. Phosphorus n.m.r. spectroscopy indicated a ca. 92 mol % yield of organophosphorus material.

Example 26

Demonstrating Synergism

The separated phosphonated dimer product of Example 22 was mixed with sodium phosphonosuccinate in varying proportions. Each of the mixtures was subjected to a calcium corrosion inhibition test (120 ppm. $Ca^{++}$, 60 ppm total inhibitor, pH 7.5, 25° C.).

Figure 2:
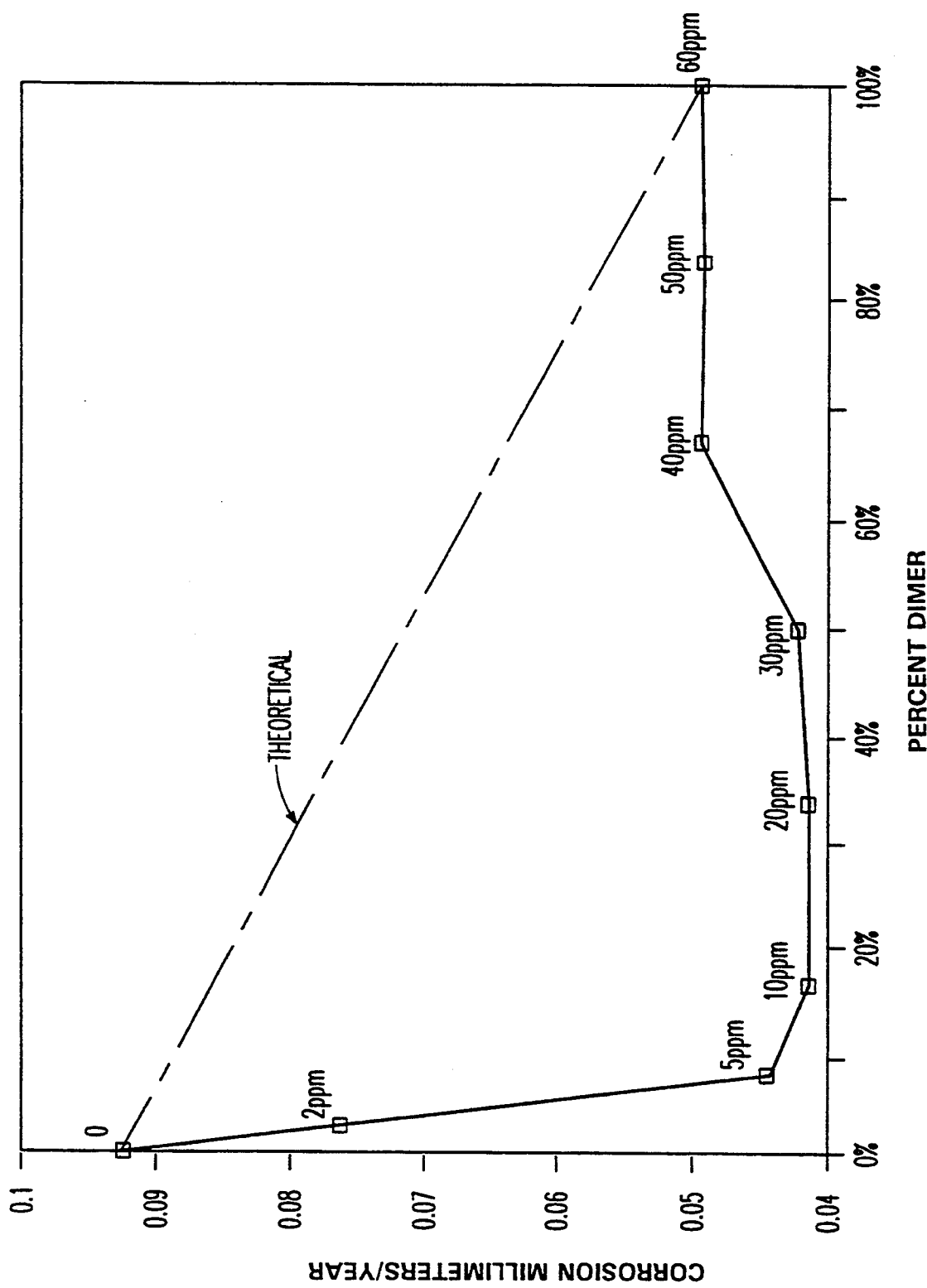
FIG. 2 shows the corrosion measured for mixtures of dimer and monomer.

The results are plotted in FIG. 2 wherein the horizontal axis is the percentage of dimer by weight based on the weight of the mixture of dimer and monomer, and the vertical axis is corrosion rate measured after 20 hours and expressed in millimeters per year. The figures shown on the plotted points are the concentration of dimer in ppm. Thus the first point on the vertical axis is the corrosion rate in the presence of 60 parts per million of the monomer, in the absence of any dimer, and the last point labelled 60 represents the corrosion rate with 60 parts per million of the dimer in the absence of any monomer. In the absence of synergism the plot should be the dashed straight line shown in FIG. 2, joining these two points. Anything below that line is evidence of synergism. Thus practically all compositions up to about 99% dimer are synergistic. It is noted that the compositions containing 5, 10, 20 and 30 parts per million of the dimer all give less corrosion than either the monomer or the dimer alone. Thus 60 parts per million of the dimer gives approximately half the corrosion observed with 60 parts per million of monomer and 10 parts per million of dimer gives substantially less corrosion than the composition with 60 parts per million of dimer. Also, as showning FIG. 2, all dimer compositions from about 8% to about 99% have synergistic corrosion rates of less than about 0.05 millimeters per year.

The present disclosure describes the embodiments of the present invention which include one or a plurality of elements and/or method steps which comprise the embodiments of the invention. Embodiments of the invention also (i) consist of and (ii) consist essentially of, the described element (s) and/or method steps.

We claim:
1. 2,3-dphosphonopropan-1-ol and its salts.
2. 2,3-diphosphonobua-1,4-diol and its salts.
3. Phosphnated dimer of maleic anhydride.

* * * * *

UNITED STATES PATENT AND TRADEMARK OFFICE
CERTIFICATE OF CORRECTION

PATENT NO. : 5,386,038
DATED : Jan. 31, 1995
INVENTOR(S) : Keith P. Davis, et al.

It is certified that error appears in the above-identified patent and that said Letters Patent is hereby corrected as shown below:

The title page should be deleted to appear as per attached.

Col. 1-22 should be deleted and substituted with col. 1-24 as per attached.

Signed and Sealed this

First Day of July, 1997

*Attest:*

BRUCE LEHMAN

*Attesting Officer*     *Commissioner of Patents and Trademarks*

United States Patent [19]

Davis et al.

[11] Patent Number: 5,386,038

[45] Date of Patent: Jan. 31, 1995

[54] WATER TREATMENT AGENT

[75] Inventors: Keith P. Davis; Peter A. T. Hoye, both of Stourbridge; Michael J. Williams, Bridgnorth; Gary Woodward, Kidderminster; Martin P. Greenhall, Northfield, all of England

[73] Assignee: Albright & Wilson Limited, West Midlands, England

[21] Appl. No.: 947,094

[22] Filed: Sep. 17, 1992

Related U.S. Application Data

[63] Continuation-in-part of Ser. No. 809,960, Dec. 18, 1991, abandoned.

[30] Foreign Application Priority Data

| Dec. 18, 1990 | [GB] | United Kingdom | 9027357 |
| May 8, 1991 | [GB] | United Kingdom | 9109861 |
| Nov. 6, 1991 | [GB] | United Kingdom | 9123501 |
| Jun. 16, 1992 | [GB] | United Kingdom | 9212748 |

[51] Int. Cl.$^6$ .................................. C07D 307/36
[52] U.S. Cl. ............................... 549/262; 562/20
[58] Field of Search .......................... 549/262; 562/20

[56] References Cited

U.S. PATENT DOCUMENTS

| 2,724,718 | 11/1955 | Stiles et al. | 260/461 |
| 2,957,931 | 10/1960 | Hamilton et al. | 260/403 |
| 3,743,688 | 7/1973 | Nicholson et al. | 260/970 |
| 3,755,504 | 8/1973 | Nicholson et al. | 260/932 |
| 4,046,707 | 9/1977 | Smith et al. | 252/180 |
| 4,183,879 | 1/1980 | Battiste | 260/932 |
| 4,351,796 | 9/1982 | Marshall | 422/15 |
| 4,590,014 | 5/1986 | Wolf et al. | 260/502.4 |

FOREIGN PATENT DOCUMENTS

| 0360747 | 3/1990 | European Pat. Off. |
| 0479465 | 4/1992 | European Pat. Off. |
| 3044214 | 6/1982 | Germany |
| 3142517 | 5/1983 | Germany |
| 660918 | 11/1951 | United Kingdom |
| 694772 | 7/1953 | United Kingdom |
| 1334365 | 10/1973 | United Kingdom |
| 1458235 | 12/1976 | United Kingdom |

OTHER PUBLICATIONS

Journal of the American Chemical Society, 92:6, Mar. 25, 1970, pp. 1685–1687.
Kogyo Kayaka Zasshi, 68, 11 (1965) (translation only).

*Primary Examiner*—Paul J. Killos
*Attorney, Agent, or Firm*—Frishauf, Holtz, Goodman & Woodward

[57] ABSTRACT

Unsaturated compounds which can be dissolved in aqueous based solvents, such as ethylenic or acetylenic carboxylate or alcohols with less than 10 carbon atoms, especially maleic and/or acrylic acid or propargyl alcohol, are reacted with alkali metal phosphite in aqueous solution at neutral or alkaline pH in the presence of free radical initiators such as persulphate to form threshold scale and corrosion inhibitors.

3 Claims, 2 Drawing Sheets

WATER TREATMENT AGENT

This application is a continuation-in-part of application Ser. No. 07/809,960, filed Dec. 18, 1991, abandoned.

The present invention relates to a novel method of phosphonation which is particularly useful for the preparation of water treatment agents that inhibit scale formation and/or corrosion of metal, e.g. iron, surfaces by aqueous systems, such as boiler water. The invention relates especially to certain novel agents which are effective when present in very low concentrations e.g. 0.1 to 100 ppm.

Such agents, on account of the minimum concentrations required for effective action, are known as threshold agents. The threshold levels are typically very much lower than would be required to achieve useful protection by a stoichiometric reagent such as a classical chelating agent.

While a large number of threshold agents are known, some of which are both scale inhibitors and corrosion inhibitors, the most effective and commercially acceptable scaling inhibitors are relatively ineffective, and are not used commercially, as corrosion inhibitors and vice versa. One group of compounds, which has been reported to show scale and corrosion inhibiting properties, is phosphonosuccinic acid and its salts. These are not, however, sufficiently effective to have enjoyed significant commercial success. The compound has been fairly expensive to make by the conventional route, which entails reacting a diester of maleic acid with dimethyl phosphite to form a phosphonosuccinic ester intermediate. The intermediate is then hydrolysed.

A particularly successful class of scale inhibitors is 2-phosphono-1,2,4-tricarboxybutane and its salts which will be referred to collectively herein as "PTCB". This is prepared by reacting the above described phosphonosuccinic ester intermediate with methyl acrylate to form the ester of the desired product, which must then be hydrolysed. This is a very expensive process on account both of the cost of the reagents and the number of steps involved. Nevertheless it has been commercially successful in competition with much cheaper products because it is effective in particularly low concentration and is said to be useful in the treatment of certain problem water systems, which cannot be effectively treated by other scale inhibitors. PTCB is not, however, normally used commercially as a corrosion inhibitor.

The most cost effective and commercially successful organic corrosion inhibitors in current use are 2-hydroxy-2-phosphonoacetic acid, $(HO)_2$ PO CHOH.COOH, and its salts, hereinafter collectively referred to as HPP. HPP has some major drawbacks as a corrosion inhibitor, in that it is relatively ineffective in the presence of zinc, which is widely used in water treatment, and in chlorinated water systems. It is not very effective as a scale inhibitor.

The phosphonation of water-insoluble long chain olefins in a non-aqueous solvent, with phosphorous acid and a free radical catalyst, has been known since 1965 from a paper by Yoshiki Okamoto and Hiroshi Sakurai in Kogyo Kayaku Zasshi 68, 11 (1965). The products have not been reported to be useful as corrosion or scaling inhibitors.

Attempts to phosphonate more reactive, water-soluble olefins such as acrylic or maleic acid with phosphorous have given negligible yields of phosphonated products.

GB 1458235 describes the preparation of certain scale inhibitors based on similar chemistry to the Japanese paper. The products are prepared, typically, by reacting hypophosphorous acid with acrylic acid. However two examples, namely examples H and I, describe an alleged reaction of phosphorous acid with acrylic acid, in the presence of a catalytic amount of potassium persulphate. The products are not specifically identified but it is implied, on the basis of their phosphorus analysis, that they are phosphonated oligomers of acrylic acid. The performances of these reaction products as scale inhibitors are mentioned in the Table 1 on p. 6 of the patent. This Table shows that they are markedly inferior to the other examples of the invention quoted in the Table and indeed not significantly more effective than commercial polyacrylic acid which is quoted as a comparative example.

The latter observation is, in fact, easily explained. We have repeated examples H and I of GB 1458235 and discovered that the reaction product is in fact polyacrylic acid. NMR confirms the absence of any P—C bonds. Presumably the Patentee had failed to remove all inorganic impurities before conducting its analysis.

The failure of phosphorous acid to give useful yields of effective phosphonated water treatment agents with unsaturated carboxylic acids, has led to the abandonment of this approach and reliance instead on the costly multi stage routes using phosphate esters and carboxylate esters.

There are many references in the art to the use of phosphono carboxylic acids in water treatment and to their preparation starting from alkylphosphites. They include U.S. Pat. Nos. 2,478,390, 2,957,931, 3,923,876, 3,959,168, 4,042,324, 4,057,511, 4,351,796 and DE-A-3,044,214.

One class of organophosphonic compounds, which have not hitherto been accessible except by very expensive multi stage syntheses of no commercial interest, and whose potentialities have therefore been overlooked, are the vicinal diphosphonates. It has been proposed to make 2,3-diphosphono propionic acid by preparing the triethyl ester of 2-phosphonoacetic acid and reacting it with triethyl phosphite and formaldehyde. The resulting ester is then saponified. The starting ester is an expensive chemical curiously which is not readily available, and the subsequent preparative steps add substantially to the cost of the product. It has also been proposed to synthesise 2,3-diphosphonobuta-1,4-dioic acid by reacting the tetraethyl ester of phosphonomaleic acid with diethyl phosphite in the presence of a base and hydrolysing the resulting ester. Again the cost of the reagents and of the ensuing steps is prohibitive.

We have now discovered that lower molecular weight (e.g. less than 10 carbon atom) olefins and acetylenes, especially water soluble hydroxy olefins and acetylenes and salts of carboxy olefins and acetylenes such as alkali metal salts, (e.g. propyolates, acrylates and/or maleates or allyl or propargyl alcohol) react with water soluble phosphites in aqueous solution, usually at elevated temperatures, in the presence of free radicals to form high yields of novel products which are generally very much cheaper to make than conventional phosphonated products such as PTCB and yet are at least comparable to the latter, and in some cases superior, in performance as scale inhibitors.

Moreover the products are also highly effective as corrosion inhibitors, especially in the presence of calcium ion, They are in many cases substantially superior to HPP in the presence of chlorine and of the hypochlorite or hypobromite commonly present in chlorinated water systems and/or in the presence of chlorine dioxide. The products are also more effective as corrosion inhibitors than HPP in the presence of zinc ions.

Particularly preferred are the reaction products obtained with maleates, acrylates or mixtures thereof, or propargyl alcohol. In the case of maleates, the product is generally a mixture of a phosphonosuccinate salt with previously unreported components which we believe include members of the homologous series of the general formula $H(CHCO_2M.CHCO_2M)_n PO_3M_2$ wherein n usually has an average value of 2 to 5 and M is a cation. Typically the mixture may comprise a phosphonosuccinate (n=1) and a substantial proportion of the higher homologues. It is also possible that hydroxy and/or sulphate substituted oligomers are formed. The mixture usually contains a small proportion of phosphate.

We have also discovered that acetylenic compounds and especially water soluble acetylenic alcohols and carboxylate salts, react with phosphite salts in the presence of free radical initiators especially persulphates, to form a range of vicinal diphosphono compounds which are of value as scaling and corrosion inhibitors.

In particular we have discovered that propargyl alcohol and its homologs react with alkali metal phosphites in the presence of, e.g., persulphates to form novel compounds which combine good scale inhibiting properties with good inhibition of corrosion especially in calcium containing systems.

According to the present invention either the product of the foregoing reaction or any of its novel components, e.g. oligomers of the above formula, may be used as scaling inhibitors or as corrosion inhibitors.

BRIEF DESCRIPTION OF THE DRAWINGS

FIG. 1 shows an ion chromatograph of the product of Example 1 showing the change in conductivity measured by the conductivity detector in microsiemens, versus time (minutes).

FIG. 2 shows the corrosion measured for mixtures of dimer and monomer.

According to a first embodiment the invention provides a method of phosphonating a preferably water-soluble or sparingly water soluble, active, ethylenically or acetylenically unsaturated compound by reacting it with a water soluble phosphite salt in the presence of sufficient of a solvent, capable of dissolving both reagents, to dissolve at least part of the reaction mixture, and of sufficient free radical to convert a substantial proportion of said unsaturated compound to a phosphonated derivative. Preferably the solvent is an aqueous based solvent.

The term "active, unsaturated compound" includes ethylenically and acetylenically unsaturated compounds in which the unsaturated bond is activated by the proximity of at least one hydroxyl, carbonyl, carboxylate, sulphonate and/or phosphonate group or by inclusion in a strained ring. Preferred examples include alkali metal maleates, acrylates, propiolates, butyne-1,4 dioates butyne-1,4-diol, propargyl alcohol, vinyl sulphonate, vinyl phosphonate, allyl alcohol, norbornene and cyclopentadiene.

Thus according to a second embodiment, the invention provides a method for the preparation of scaling and/or corrosion inhibitors which comprises heating: (1) at least one water soluble carboxy, hydoxy, sulphono or phosphono olefin having the general formula $R_2C=CR_2$ where at least one R group is a COOM, $R_2C=CR$ $CH_2OH$, $SO_3M$ or $PO_3M_2$ group and each of the other R groups may be the same or different and each represents hydrogen or a hydrocarbon or substituted hydrocarbon group, or in which two of the R groups together form a cycloalkyl or cycloalkenyl group, or part thereof, and M is a cation such that the salt is water soluble with (2) a water soluble salt of phosphorous acid; in the presence of (3) sufficient of an aqueous based solvent to dissolve at least part of each of the reagents; and (4) sufficient free radicals to form a phosphonated oligomer of said olefin.

According to a third embodiment our invention provides a method of preparing vicinal diphosphono compounds which comprises reacting an acetylenic compound with a phosphite salt in the presence of sufficient free radical to convert a substantial proportion of said acetylenic compound to a vicinal disphosphono compound, preferably in an aqueous based solution.

Preferably the acetylenic compound is water soluble, e.g, an acetylenic alcohol or carboxylate salt, especially one having less than 10, more particularly less than 6, e.g. less than 5 carbon atoms. We have found that propargyl alcohol reacts according to our invention to give a particularly effective and novel combined scaling and corrosion inhibitor, namely 2,3-diphosphonopropanol, usually formed in admixture with some phosphonated oligomers of propargyl alcohol. Other novel and useful compounds which may be prepared by the method of our invention and which are included in our invention comprise compounds of the formula.

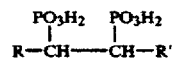

Where R is a hydroxy and/or carboxy substituted alkyl group having a total of 1 to 5 carbon atoms and R' is hydrogen, a carboxylate group, a hydrocarbon group having from 1 to 4 carbon atoms or an R group, and their salts. Preferably the compound has a total of less than six carbon atoms.

The invention according to a fourth embodiment provides novel phosphonated oligomers of active olefins which oligomers have the formula $$H[CHRCHR]_n - PO_3M_2$$

wherein at least one R group in each unit is a COOM, $CH_2OH$, sulphono or phosphono group and the other R group which may be the same as, or different from, the first R group, is hydrogen or a COOM, hydroxyl, phosphono, sulphono, sulphato, $C_{1-7}$alkyl, $C_{1-7}$alkenyl group or a carboxylate, phosphono, sulphono, sulphato and/or hydroxy substituted $C_{1-7}$alkyl or $C_{1-7}$alkenyl group, and each M is a cation such that the phosphonated oligomer is water soluble and n is greater than 1, e.g. up to 6. Preferably n has value less than 5 e.g. 1.2 to 3.

This invention also provides phosphonated cooligimers of the above formula, but in which the $[CHRCHR]_n$ chain contains at least two [CHRCHR] groups derived from different monomers and in which n has a total value of at least 3. For example we include a phosphonated trimer or higher cooligomer of maleate and acrylate containing at least one [$CH_2CHCOOM$] and at least one [CHCOOM CHCOOM] group.

The invention, according to a preferred embodiment, provides a novel phosphonated oligomer or mixture of phosphonated oligomers of maleic acid, of the formula $H(CHCO_2M.CHCO_2M)_nPO_3M_2$ where n is greater than 1 and M is a cationic species such that the compound is water soluble, and especially mixtures of such compounds with phosphonosuccinic acid or its water soluble salts, often in a minor proportion by weight based on the total weight of the solvent-free mixture.

It is particularly preferred, according to the invention, to use reaction products which comprise: up to 50% by weight of a phosphonosuccinate based on the weight of the solvent-free composition; a phosphonated dimer of maleate; optionally a minor proportion by weight, relative to the weight of dimer, of higher phosphonated oligomers of maleate; and from 0.5 to 5% by weight of alkali metal phosphate.

According to a further preferred embodiment the invention provides a novel phosphonated oligomer of a water soluble acrylate comprising an average of from 2 to 15 acrylate units per mole and exhibiting at least one NMR $^{31}P$ resonance characteristic of a C—P bond.

According to another embodiment our invention provides a novel vicinal diphosphonate of the formula $RCHPO_3M_2$ $CHR'PO_3M_2$ where R is a hydroxy, carboxy, phosphono, sulphato and/or sulphono substituted alkyl group having up to 5 carbon atoms, R' is hydrogen, a carboxylate, a $C_{1-4}$ hydrocarbon or an R group and H is hydrogen or a cation or cationic group.

The invention further provides the use of the reaction products and novel phosphonated oligomers and vicinal diphosphonates according to the invention as scale inhibitors or as corrosion inhibitors in aqueous systems, or as detergent builders or chelating agents for metals.

In particular the invention provides a method for the treatment of potentially scale forming aqueous systems, or of potentially corrosive aqueous systems, to inhibit scaling or corrosion respectively, which comprises adding thereto a threshold amount (e.g. an effective amount less that 100 ppm by wt.) of a novel compound or mixture of compounds according to the invention.

The invention further provides a method for the preparation of a compound or mixture of compounds of the invention, which comprises reacting together water soluble salts of maleic and phosphorous acids in aqueous solution and in the presence of an effective amount of a free radical initiator, and preferably in an aqueous based solvent.

Examples of acetylenically unsaturated compounds which may be used in the method of our invention include propargyl alcohol, propiolates, buta-2,3-yne-1,4-dioates, and other acetylenically unsaturated alcohols, carboxylate salts and hydroxycarboxylate salts having less than 10 carbon atoms.

The novel vicinal diphosphono compounds of the present invention may be prepared by reacting an aqueous solution of the acetylenically unsaturated alcohol and/or water soluble salts of the carboxylate reagent, as the case may be, with a phosphite, usually an alkali metal phosphite such as sodium or potassium phosphite in the presence of free radicals. The free radicals are typically provided by adding sodium persulphate or hydrogen peroxide, in sufficient quantity to convert a substantial proportion, e.g., more than 50%, preferably more than 60% of the acetylenic compound into the diphosphono compound. Instead of water it is possible to use other aqueous based solvents such as aqueous ethanol, aqueous methanol, aqueous dioxan or aqueous acetone. Such solvents are preferred where the acetylenic compound is only sparingly soluble in water.

The reaction may give rise, in addition to the diphosphono derivative, to some phosphonated oligomers of the acetylenic reagent. These oligomers, and reaction products containing them, have valuable scale and corrosion inhibiting properties and are included in our invention. The reaction may additionally form a proportion (usually minor) of geminal diphosphonate. The reaction product also, typically, contains some phosphate. The mixtures of vicinal diphosphonate, geminal diphosphonate, phosphonated oligomers and/or inorganic phosphate show synergistic activity.

Important differences between the preferred methods of the present invention, and prior art attempts to prepare phosphonates from olefins using phosphorous acid, include: the use of an aqueous based solvent and the use of salts rather than free acids. The reaction preferably is run at neutral or alkaline pH. Elevated temperatures are preferred and the amount of free radical initiator required is often substantially more than is usually used in free radical catalysed reactions. The initiator is preferably dosed continuously or intermittently to the reaction mixture to the extent required to keep the reaction going to completion.

The method of the invention preferably employs alkali metal salts of any acid reagents, e.g. an alkali metal propiolate, acrylate, methacrylate and/or maleate and a di-alkali metal phosphite in each case the alkali metal is preferably sodium, but other cations which form soluble phosphites and which do not interfere with the reaction may be used. Examples include calcium, potassium, lithium and magnesium. Phosphonium (e.g. tetra alkyl or tetrakis hydroxymethyl), ammonium and substituted ammonium such as tetramethyl ammonium and/or mono-, di- and/or tri- and ethanolammonium may also be used, but are not preferred.

The proportion of phosphite to unsaturated compound is preferably substantially stoichiometric, i.e. equimolar in the case of ethylenically unsaturated compounds or 2:1 molar in the case of acetylenes. A small excess of either reagent may be present, however substantial excesses of the phosphite are generally undesirable. Excesses of the unsaturated compound generally result in the formation of unphosphonated oligomers. Since the latter are usually effective water treatment agents in their own right, and are often useful synergists with the phosphonated products of this invention, comparatively large excesses of the unsaturated agent can be tolerated.

Preferably the mole ratio of ethylenically unsaturated compound to phosphite is from 1:5 to 15:1, usually 1:1 to 3:1, especially 1.3:1 to 2.5:1 e.g. 1.5:1. Generally, higher proportions of phosphite to unsaturated compound will be required to phosphonate acetylenes. For instance the proportion of phosphite to acetylene may be from 10:1 to 1:10, usually 5:1 to 1:8, especially 3:1 to 1:5, e.g. 2.5:1 to preferably 2:1 to 1:1.

The unsaturated compound is preferably a maleate, acrylate or a mixture thereof or a propiolate or allyl or propargyl alcohol. Other olefins and acetylenes include methacrylate, vinyl sulphonates vinyl phosphonates, 2,3-butyne-1,4-diol, butyne-1,4-dioates, 2,3-butyne-1-ol-4-oates, norbornene, vinyl acetate 2,3-butene-1,4-diol and 2,3-butene-1-ol-4-oates. Compared with maleates, fumerates have been found comparatively unreactive.

We prefer to carry out the preparations at a concentration of the reagents at which the reaction mixture will just remain fully dissolved and stirrable at the reaction temperature.

The reaction may, however, be carried out in the presence of sufficient solvent to dissolve only part of the reagents, but sufficient, preferably, to form a stirrable slurry. For instance amounts of total solids may be from 0.5 to 96% by weight of the reaction mixture, more usually 1 to 95% e.g. 10 to 90%, especially 20 to 85, preferably 35 to 80%, more preferably 50 to 80%, for example 60 to 78% or 70 to 75%.

The desired concentration may conveniently be achieved by dissolving the reagents in, e.g. water, and evaporating down, e.g. until the mixture is still just stirrable, or by heating a mixture of phosphorous acid and the unsaturated compounds and neutralising with hot concentrated base such as sodium hydroxide, prior to adding the free radical initiator.

The reaction requires a source of free radicals for the system, e.g. an ammonium or alkali metal persulphate or peracetate, hydrogen peroxide, a hydroperoxide, chlorine dioxide, sodium chlorate, sodium hypochlorite, organotin hydrides, azo compounds such as 4,4'-azobiscyanovaleric acid, electrolysis, ultra violet or other ionising radiation or ultrasound, or any combination of the foregoing. With the preferred use of peroxide as a free radical source, phosphonated product yields of 90% have been obtained and the reaction product can be used directly, without purification.

The amount and rate of formation of free radical generated determines the extent to which the reaction may proceed and the time required.

The amount of free radical initiator used should be sufficient to take the reaction to completion in reasonable time (e.g. within 0.25 to 24 hours). Smaller amounts may be used if incomplete reactions can be tolerated. Generally the quantity of free radical required is substantially greater than in normal free radical catalysed reactions. Excess free radical source is, however, preferably avoided on economic grounds and to minimise contamination of the product. Generally the more water present, the more free radical is required in order to complete the reaction. Also, more elevated temperatures may permit the reaction to proceed with less addition of free radicals. We therefore prefer to use a concentrated reaction mixture e.g. at least 60% and preferably more than 70% total solids. Under these conditions the amount of initiator required is typically from 1 to 10 mole % e.g. 2 to 8 and preferably from 3 to 6 mole based on the unsaturated reagent. However if the reaction is performed in a more dilute system, and/or at lower temperatures, higher amounts of initiators such as sodium, potassium or ammonium persulphate may be required, typically from 10 to 30 by weight of the unsaturated reagent, e.g. 20 to 25.

The reaction mixture is preferably at a pH at least neutral, or slightly alkaline. Acid pH should be avoided. Typically pH should be above 5 and especially above 5.5 preferably above 6 more preferably above 6.5 e.g. 6.8 to 10 most preferably 7 to 9 at least initially, although the pH may be allowed to drop below 7 as the reaction approaches completion.

The reaction normally precedes in an aqueous based solvent which is typically water, provided the selected reagents are sufficiently soluble. Water miscible organic solvents may be included, where required for more sparingly soluble reagents. The solvent should contain sufficient water to dissolve the phosphite to a substantial extent. The organic solvent may for example comprise methanol, ethanol, iso-propanol, ethylene glycol, propylene glycol, a water soluble oligomer of ethylene or propylene glycol such as diethylene glycol, a water soluble mono- or di- ether of ethylene or propylene glycol or of an oligomer thereof, such ethylene glycol monomethyl ether, ethylene glycol dimethyl ether, diethylene glycol monomethyl ether or diethylene glycol mono ethyl ether, glycerol, a water soluble glyceryl ether, acetone, and/or dioxan. The requirement to dissolve the phosphite and the olefin or acetylene in the same aqueous based solvent is the main limitation on choice of unsaturated reagent. In cases of difficulty it may be possible to carry out the reaction in anhydrous dioxan.

The reaction mixture generally requires heating for at least part of the reaction time in order to initiate and maintain the reaction. Preferably temperatures above 60° C., more preferably above 80° C., e.g. 90° C. to the boiling point of the mixtures are used, and maintained for from 30 mins to 8 hours in order to complete the reaction. Higher temperatures, e.g. under pressure, for example in an autoclave, may be advantageous. Typically the temperature is between 50° and 250° C. e.g. below 200° C. and preferably below 150° C. Optimum temperatures are usually in the range 95°–140° C. e.g. 100°–130° C.

We prefer that the reaction should be carried out under an inert atmosphere, e.g. nitrogen. This helps to improve the yield of product.

The reaction may be carried out batchwise, semi-continuously or continuously e.g., in a pipe reactor. The free radical source may all be added initially or, preferably, in a plurality of additions, or continuously or semi-continuously throughout the reaction.

To maximise the yield of phosphonated product it is sometimes necessary to add the unsaturated reagent, continuously or intermittently during the reaction period to an aqueous solution of the phosphite.

The product typically contains a proportion, e.g. in the case of maleates, up to about 40%, by weight thereof, of the phosphonate monomer (e.g. phosphonosuccinate) the remainder comprising a phosphonated dimer possibly with small amounts of higher homologues, and inorganic salts such as phosphates.

In the most preferred method of preparing a water soluble organic phosphonate by reacting a water soluble olefinic or acetylenic carboxylate salt or alcohol with a water soluble phosphite salt in the presence of water, the quantity of water used is less than about 50% by weight which is generally less than that required fully to dissolve the reagents at room temperature, the temperature is sufficiently elevated to provide a stirrable reaction mixture and hydrogen peroxide (or other peroxide source) is used and is present in an amount effective to maintain the reaction.

As noted, other peroxides than hydrogen peroxide can be used, also free radical sources generally can be used.

In this preferred embodiment, the amount of water present initially, is preferably less than 40% by weight based on the total weight of the reaction mixture, e.g., less than 35% especially less than 32%. Generally we prefer that the amount of water be greater than 10%, preferably greater than 15% e.g., greater than 20%, most preferably more than 25% by weight based on the total weight of the reaction mixture. Thus, water is preferably used in an amount of 10% to 40% by weight and most preferably 25–32% by weight.

The proportion of peroxide is typically an effective amount up to 25% molar, based on the unsaturated compound. We prefer to use only sufficient peroxide to initiate the reaction to a substantial extent, e.g. to provide yields of phosphonated product greater than 70% molar based on the unsaturated compound preferably greater than 80% molar, e.g. greater than 85% molar. This minimum amount of peroxide depends on the amount of water and is generally reduced as the amount of water is reduced. For example at 30% wt/wt water, yields of about 90% can be obtained using between 4 and 6 mole % of peroxide based on the unsaturated compound.

The temperature of the reaction is preferably above 60° C. more preferably above 70° C., typically at the boiling point of the mixture. Rapid refluxing and agitation favour the reaction, and we therefore prefer to carry out the process under conditions which promote rapid evaporation such as a wiped film or spray evaporator, preferably incorporated in a loop reactor.

Thus the reaction mixture may be continuously recycled through an evaporator and reagents and initiator continuously or intermittently added.

The ratio of unsaturated compound to phosphite typically determines the proportion and mean degree of polymerisation of any dimer or higher polymers formed. We prefer to use molar ratios greater than 1 but preferably less than 2, e.g. 1.2 to 1.5, e.g. 1.3.

We have found high pH an advantage. Generally the pH should be above 5, suitably above 7, preferably above 7.5, more preferably above 8, especially above 8.5 to 9.5, e.g. 9 to 10. Although even higher pH's can be used, at a pH much above 10 (e.g. a pH of 12) the corrosiveness of the solution that results reduces the practicality of using such a high pH especially if direct use of the reaction mixture is contemplated.

If it is desired to purify the product, e.g., by separating phosphonated monomer from the phosphonated oligomers, it is possible to esterify the products to form, e.g., methyl esters and distill off the phosphonated monomer. However, an advantage of the present method is that expensive purification of the reaction product is generally not necessary. The mixture is an effective water treatment agent in its own right, and its efficiency is enhanced by synergism.

We believe that one reason for the high useful purity yields available with this most preferred method wherein peroxide is the free radical source, is based in the low reactivity of the trans isomer of the olefin being chemically activated, e.g. by carboxylate and/or hydroxyl groups. More specifically, as shown in Example 22 below, a high yield, high purity product is formed when the olefin is a maleate (cis isomer) and hydrogen peroxide is used as the free radical source. Similar results are not possible with fumarate (trans isomer). In fact, we have found that trans isomers tested have low activity especially when the source of free radicals is persulfate. With peroxide as a source of free radicals, we have been able to achieve a yield of only about 30% with fumarate (trans isomer) and the proportion of monomer to dimer and other higher molecular weight material appears to be much larger than in the case of maleates (cis isomer).

The unexpectedly good results obtained using the peroxide free radical source as compared with persulfate, appears to be partly due to the isomerization of part of the maleate to fumarate when persulfate is used and the lack of such isomerization with peroxide. As noted above, fumarates have very little if any reaction with persulfates leaving fumarates as unreacted impurities in the reaction mixture along with sulphate residues.

The phosphonation reaction product of maleate salts using peroxide contains a mixture of salts of phosphonated dimer of maleic acid (1-phosphono-1,2,3,4-tetracarboxybutane) and phosphonosuccinate in sufficiently pure form that it can be used directly, without further purification.

In view of the fact that phosphonosuccinic acid and its salts are relatively poor scale and corrosion inhibitors, we attribute the strikingly enhanced performance of our novel reaction products, or at least those derived from maleates, to the presence either of higher homologues or of chemically modified oligomers, e.g. hydroxyl or sulphate derivatives and/or to the presence of inorganic phosphate. We believe that certain of these homologues may be inherently superior to phosphonosuccinates as scale and corrosion inhibitors. We also believe that there is synergistic action between the components of our novel reaction products.

We have found that a synergism is shown with a mixture of phosphonosuccinic acid and the novel phosphonate dimer of maleic acid produced by the phosphonation of maleic acid using the peroxide free radical source. The synergism is shown for substantially all mixtures although particularly marked synergism is shown for mixtures containing the phosphonate dimer of maleic acid in amounts of 8% to 65% by weight based on total weight of the mixture of phosphonosuccinate and dimer. Particularly preferred is a mixture containing from 10% to 60% by weight of the dimer based on the mixture weight, and more especially 12–50%. The reaction product contains about two-thirds phosphonosuccinate and one-third of the dimer, which is in the middle of the range for particularly marked synergism.

There is evidence that some higher oligomers are also present which can be represented as $H_2PO_3[C(COOH)-C(COOH)]_m H$ where m is an integer or $H_2PO_3[C(COOH)_n H$ where n is an even numbered integer (e.g. 1-phosphono-1,2,3,4,5,6-hexacarboxyhexane). However, these are present in relatively small quantities which do not require removal for use of the reaction product.

The compounds or mixtures of our invention are of particular value as corrosion inhibitors in systems containing calcium ions and may also be used in conjunction with zinc salts.

The products are effective in the presence of chlorine, chlorine dioxide, bromine, hypochlorite, hypobromite and other oxidising biocides. They may therefore be used to treat chlorinated water systems or systems sterilised by other oxidising agents. They are useful in cooling water treatment, treatment of industrial process water, boiler water treatment, desalination plant and for treating water used or produced in oil wells including injection water, produced water, and water used for hydrostatic testing of pipelines.

They are also of value as detergent builders or auxiliary builders, e.g. in conjunction with zeolites, or as metal chelating agents, e.g. in metal extractions. They may be used in aqueous based functional fluids such as hydraulic fluids, lubricants, cutting fluids and oil field drilling muds.

For example the compounds and mixtures of the invention may be used in squeeze treatment of all wells in conjunction with calcium salts, or may be added to drilling muds or to oilfield injection water, produced water or water for hydrostatic testing, as well as to various industrial cooling waters and process waters and to water for use in central heating systems. They are especially effective in preventing barium sulphate scale.

Squeeze treatment of boreholes, e.g. to prevent formation of $BaSO_4$ scale, typically entails impregnating the formation in the environs of the hole with a calcium salt of the inhibitor, which is subsequently leached into any aqueous system circulating in the hole to provide controlled slow release.

For example in oil wells the hole is flushed out with aqueous surfactant to provide a water wettable surface and then impregnated with a solution of the inhibitor. The calcium salt is formed in situ either by calcium in the formation, where the latter comprises limestone, or by subsequent treatment of the hole with an aqueous calcium salt, e.g. where the formation comprises sandstone.

The compounds and mixtures are useful in treating chlorinated water systems for which many threshold agents are ineffective. Effective concentrations may typically range from 0.1 to 50 ppm depending on the nature of the aqueous system preferably 0.5 to 20 ppm especially 1 to 10 ppm e.g. 1.5 to 4 ppm.

Products according to the invention may be used in combination with one another, and/or in conjunction with other water treatment agents including: surfactants, such as anionic surfactants (e.g. $C_{10-20}$ alkyl benzene sulphonates, $C_{10-20}$ olefin sulphonates, $C_{10-20}$ alkyl sulphates, $C_{10-20}$ alkyl 1 to 25 mole ether sulphates, $C_{10-20}$ paraffin sulphonates, $C_{10-20}$ soaps $C_{10-20}$ alkyl phenol sulphates, sulphosuccinates, sulphosuccinamates, lignin sulphonates, fatty ester sulphonates, $C_{10-20}$ alkyl phenyl ether sulphates, $C_{10-20}$ alkyl ethanolamide sulphates, $C_{10-20}$ alpha sulpho fatty acid salts, $C_{10-20}$ acyl sarcosinates, isethionates, $C_{10-20}$ acyl taurides, $C_{10-20}$ alkyl hydrogen phosphates), non-ionic surfactants (e.g. ethoxylated and/or propoxylated $C_{10-20}$ alcohols, ethoxylated and/or propoxylated $C_{10-20}$ carboxylic acids, alkanolamides, amine oxides, and/or $C_{10-20}$ acyl sorbitan and/or glyceryl ethoxylates) amphoteric surfactants (e.g. betaines, sulphobetaines, and/or quaternised imidazolines), and/or cationic surfactants (e.g. benzalkonium salts, $C_{10-20}$ alkyl trimethyl ammonium salts, and/or $C_{10-20}$ alkyl trimethyl or tris(hydroxymethyl) phosphonium salts); sequestrants, chelating agents, corrosion inhibitors and/or other threshold agents (e.g. sodium tripolyphosphate, sodium ethylenediamine tetracetate, sodium nitrilo triacetate, tetra potassium pyrophosphate, acetodiphosphonic acid and its salts, ammonium trismethylene phosphonic acid and its salts, ethylenediamine tetrakis (methylene phosphonic) acid and its salts, diethylenetriamine pentakis (methylene phosphonic) acid and its salts); tolyltriazole and mixtures of nitrate, benzoate, HHP and/or PTCB) biocides (e.g. tetrakis (hydroxymethyl) phosphonium salts, formaldehyde, glutaraldehyde); oxidising biocides and/or bleaches (e.g. chlorine, chlorine dioxide, hydrogen peroxide, sodium perborate); foam controlling agents such as silicone antifoams; oxygen scavengers such as hydrazines and/or hydroxylamines; pH controlling and/or buffering agents such as amines, borates, citrates and/or acetates; chromium salts; zinc salts; and/or other water treatment agents such as polymeric dispersants and coagulants including polymaleic, polyacrylic and polyvinylsulphonic acids and their salts, starches and/or carboxy methyl cellulose, and/or molybdates. The invention provides formulations comprising an effective amount of a product of the invention as aforesaid and any of the aforesaid known water treatment agents. Such formulations may, for example, contain from 5 to 95% by weight of a product of the invention and from 5 to 90 by weight of one or more of any of the aforesaid water treatment agents.

Detergents according to this invention may comprise 2 to 70% preferably 3 to 50% e.g. 5 to 20% by weight surfactant and 5 to 60%, preferably 10 to 45% e.g. 15 to 30% by weight total builder, the major portion of any balance being typically a carrier, solvent or diluent.

The builder may consist of a phosphono or diphosphono product according to this invention. Alternatively the builder may comprise such a product together with one or more other builders such as zeolite, sodium tripholyphophate, potassium pyrophosphate sodium or potassium carbonate, sodium citrate, sodium nitrilotriacetate, sodium silicate and or sodium ethylene diamine tetracetate. Thus the product of the invention may constitute from 1% to 100% of the total builder, e.g. 5 to 90% especially 10 to 80%. The balance may comprise an inert solid such as sodium sulphate, or a liquid medium such as water or a low molecular weight polyethylene glycol. The detergent may additionally comprise: up to 5% by weight, e.g. 0.01 to 2% by weight, of optical brightener; up to 5% by weight e.g. 0.01 to 2% by weight of soil suspending agent such as sodium carboxymethyl cellulose; and up to 6%, more usually up to 2%, by weight, each, of perfume, dye enzyme, bleach, buffers and of the conventional ingredients of solid or liquid detergent composition.

The invention will be illustrated by the following examples. All preparations were carried out under an atmosphere of nitrogen.

The evaluations were performed in accordance with the following test methods:

Test Method No. 1

Synthetic seawater brine having total $CO_2$ content of 100 mg.$l^{-1}$ is prepared to the following formulation:

| Component | Formulation Concn. (g.$l^{-1}$) |
|---|---|
| NaCl | 49.06 |
| $MgCl_2.6H_2O$ | 22.21 |
| $Na_2SO_4$ | 8.18 |
| $CaCl_2.2H_2O$ | 3.074 |
| KCl | 1.390 |
| KBr | 0.202 |
| $NaHCO_3$ | 0.191 |
| pH | 8 |

500 ml of synthetic seawater concentrate and the appropriate amount of a 0.5 gm/liter stock solution of the inhibitor are heated to, and maintained at, 80° C. and pH adjusted to 8.00+0.01. 0.125 gm of precipitated calcium carbonate, having 60% by weight aragonite and 40% calcite, is added and the pH monitored for 60 minutes.

If no drop in pH greater than 0.1 units is observed the inhibitor is providing 100% inhibition of aragonite scaling. The test is repeated until the minimum (threshold) concentration for 100% inhibition has been determined.

Test Method No. 2

Synthetic formation water is prepared, having the formula:

| | |
|---|---|
| NaCl | 110.08 g |
| $Na_2SO_4$ | 16.265 g |
| $NaHCO_3$ | 5.25 g |
| $MgCl_26H_2O$ | 35.55 g |
| $CaCl_2H_2O$ | 9.535 g |
| $SrCl_26H_2O$ | 0.26 g |
| KCl | 2.955 g |
| $H_3BO_3$ | 0.43 g |
| pH | 7.8 |

The synthetic formation water is seeded with precipitated calcium carbonate and pumped through a 1/16 inch bore capillary tube at 90° C. and at a rate of 25 ml/min until the pressure across the tube reached 5 psi. The inhibitor is observed to determine any continuing rise. The minimum concentration of inhibitor to stop further rise of pressure is determined.

Test Method Nos. 3 and 4

These tests are based on the measurement of linear polarisation using an "ELECTROCHEMICAL INTERROGATOR" to determine the corrosion current. The rate of corrosion is expressed in mm per year of iron lost from the surface of the carbon steel work electrode. The auxiliary electrode is platinum and the reference electrode saturated calomel. The calcium test (Method 3) used medium containing 120 ppm Ca++ and 213 ppm Cl− at a pH of 7.5 and a temperature of 25° C.

The zinc test (Method 4) used a medium containing 20 ppm Zn++, 200 ppm Cl−, a pH of 7.5 and a temperature of 25° C.

Both tests used 60 ppm inhibitor (expressed as the acid) and swept from −20 mv to +20 mv with respect to rest potential in minute.

Example 1

A solution of maleic acid (1.74 Kg, 15M) and sodium hydroxide (1.2 Kg, 30M) in water (4.5 L) was added over 1 hr 40 min to a stirred refluxing solution (102°–103° C.) of $H_3PO_3$ (820 g, 10M) and sodium hydroxide (800 g, 20M) in water (2 L). Over this period a solution of ammonium persulphate [684 g, 20 mol % (w.r.t. maleic acid)] in water (1.3 L) was added dropwise. After these additions the reaction mixture was refluxed for 15 mins and then a further 5 mol ammonium persulphate solution (171 g in 330 ml water) was added dropwise over 30 min. After a further 30 min reflux the solution was allowed to cool slowly. A $^{31}P$ n.m.r. spectrum of this reaction mixture ($D_2O$) showed that 88% of the phosphorous acid had reacted and that 5% had been oxidised to $H_3PO_4$. 40% by wt. of the organo-phosphonic acids present was phosphonosuccinic acid (n=1) and 60% by wt. higher homologues with n > 1. A 1H.n. spectrum indicated that approximately 85% of the disodium maleate had reacted. The average value of n is therefore approximately 1.5. The product contains about 2% by weight of sodium phosphate.

Example 2

A solution of maleic acid (174 g, 1.5M) and sodium hydroxide (120 g, 3M) in water (450 ml) was added dropwise over 1 hr 20 min to a stirred refluxing solution of $H_3PO_3$ (82 G, 1M) and sodium hydroxide (80 g, 2M) in water (200 ml). During this period sodium persulphate (71.4 g, 20 mol % w.r.t. maleic acid) was added in portions to the reaction mixture. After these additions the solution was refluxed for 15 minutes and then another 5 mol % of sodium persulphate (17.9 g) was added over 30 mins. The solution obtained was refluxed for a further 30 mins and then allowed to cool to room temperature. $^{31}P$ and $^1H$ n.m.r. spectroscopy indicated a product identical to the first example.

Example 3

A solution of acrylic acid (72 g, 1M) and sodium hydroxide (40 g, 1M) in water (200 ml) was added dropwise over 0.75 h to a stirred refluxing solution of phosphorous acid (8.2 g, 0.1M) and sodium hydroxide (8 g, 0.2M) in water (100 ml). During this time sodium persulphate (47.6 g, 20 mol % wrt to the acrylic acid) was added portionwise. The solution obtained was boiled for 0.25 h and then sodium persulphate (10 g) was added over 0.25 h to this boiling solution. $^{31}P$ n.m.r. spectral data indicated that 30 mol % of the phosphorous acid had been oxidised to phosphate; the remainder had reacted with the acrylic acid to produce a phosphonate material. A $^{13}C$ n.m.r. spectrum indicated that all the acrylate had reacted. The product must therefore contain ca. 14 acrylic acid units to each phosphorus.

Example 4

A solution of acrylic acid (9 g, 0.125M), maleic acid (14.5 g, 0.125M) and sodium hydroxide (15 g, 0.375M) in water (250 ml) was added dropwise over one hour to a stirred refluxing solution of phosphorous acid (10.3 g, 0.125M) and sodium hydroxide (10 g, 0.25M) in water (100 ml). During this period sodium persulphate (11.9 g, 20 mol % wrt olefins) was added portionwise. The solution obtained was refluxed for 0.25 hr and then allowed to cool to room temperature. A $^{31}P$ n.m.r. spectrum indicated that 67 mol % of the $H_3PO_3$ had reacted to give material containing PC bonds and 13 mol % had been oxidised to phosphate. $^{13}C$ and $^1H$ n.m.r. spectral data indicated that all the acrylic acid and ca. 90% of the maleic acid had reacted. Therefore the material formed has 1.5 acrylic acid and 1.3 maleic acid units to each phosphorus.

Example 5

The product of Example 1 was tested for scale inhibition in comparison with sodium phosphonosuccinate and PTCB using the aragonite test (Test Method No 1 above). The test results are listed in Table 1, expressed as ppm of the 100% inhibitor. The test was repeated in the presence of 3 ppm chlorine and again after the product had been exposed to 3 ppm chlorine dioxide for 1 hour at 60° C. with identical results.

The results of a test of tube blocking with aragonite scale (Test Method No 2 above) are also recorded in Table 1.

The product was steam distilled and no phosphorus was detected in the distillate.

TABLE 1

| Test | Example 1 | Phosphonosuccinate | PTCB |
|---|---|---|---|
| Aragonite (Test No 1) | 1.4–1.5 | 4.7–4.8 | 1.0–1.1 |
| Tube Blocking (Test No 2) | 0.5–0.6 | 1.0–1.4 | 0.8–1.0 |

Example 6

Vinyl sulphonic acid (100 g of a 30%w/w solution of the sodium salt, 0.23M) was added dropwise over 0.25 h to a refluxing stirred solution of phosphorous acid (6.28 g, 0.07M) and sodium hydroxide (6.12 g, 0.15M) in water (100 ml). During this period sodium persulphate (10.9 g, 20 mol % w.r.t. vinyl sulphonic acid) was added portionwise. The reaction mixture was boiled for a further 0.5 h. $^{31}P$ n.m.r. analysis of the reaction mixture indicated that 82 mol % of the phosphorous acid had reacted to give organo-phosphorus materials. All the remaining phosphorous acid had been oxidised to phosphate. $^{13}C$ n.m.r. data indicated that all the vinyl sulphonic acid had reacted and therefore that the product contained on average 3.7 vinyl sulphonic acid groups to each phosphorus.

Example 7

A solution of allyl alcohol (58 g, 1M) in water (500 ml) was added dropwise over 5 h 10 min to a stirred refluxing solution of phosphorous acid (82 g, 1M) and sodium hydroxide (80 g, 2M) in water (200 ml). During this period sodium persulphate (59.5 g, 25 mol % w.r.t. the allyl alcohol) was added portionwise. The product obtained as analysed by $^{31}P$ and $^{13}C$ n.m.r. spectroscopy. This indicated that ca. 71 mol % of the phosphorous acid had reacted and ca. 14 mol % had been oxidised to phosphate. All the allyl alcohol had reacted, therefore the product obtained contains an average of 1.4 allyl alcohol units to each phosphorus.

Example 8

A solution of vinyl phosphonic acid (19.3 g 0.18M) and sodium hydroxide (14.3 g, 0.36M) in water (200 ml) was added dropwise over 2.75 h to a stirred refluxing solution of phosphorous acid (5.1 g, 0.062M) and sodium hydroxide (4.93 gm. 0.123 m) in water (100 ml). A solution of sodium persulphate (8.8 g, ca. 20 mol % w.r.t. the vinyl phosphonic acid) in water (65 ml) was added simultaneously over the same period. After these additions the reaction mixture was boiled for ca. 1.5 h and then a solution of sodium persulphate (4 g) in water (25 ml) was added dropwise over 0.5 h. $^{31}P$ n.m.r spectroscopy of the reaction mixture indicated that all the vinyl phosphonic acid had polymerised and that ca. 25–30% of the phosphorous acid had been incorporated into the product polymeric mixture. The remaining unreacted phosphorous acid had been oxidised to phosphate.

Example 9

A solution of maleic acid (116 g, 1M), sodium hydroxide (106 g, 2.65 m) and phosphorous acid (12.5 g, 0.15M) in water (450 ml) was heated to 95° C. in a boiling water bath. Sodium persulphate (60 g, 0.25M) was added in small portions at 5 minute intervals to the well stirred solution over a period of eight hours. A further portion of sodium hydroxide (5.5 g) was added after 5 hours to keep the solution alkaline and prevent rapid oxygen evolution when the persulphate was added. Analysis of the product as in Example One showed that 17% of the phosphorous acid used had been converted to phosphate 9% remained unreacted, 26% had been converted to phosphonosuccinic acid and the remainder to polymeric species. The average n was 5.2.

Example 10

A solution of maleic acid (110 Kg, 950M) and sodium hydroxide (170 Kg of a 47% aqueous solution 2000M) on water (255 Kg) was added slowly over 3 h to a stirred refluxing solution of phosphorous acid (60 Kg, 732M) and sodium hydroxide (125 Kg of a 47% solution, 147M) in water (90 Kg). 100 L of a solution of sodium persulphate (67.9 Kg, 285M (30 mol % w.r.t, maleate)) in water (116 Kg) (150 L in total) was added simultaneously over the same period. The reaction mixture was refluxed for 1 h after which the remaining sodium persulphate solution (50 L) was added over 0.5 h. Refluxing was continued for a further 3 h after which the reaction was allowed to cool. Analysis of the product indicated a very similar composition to that described in Example One, ca. 84 mol % of the phosphorus acid had reacted and 12 mol % had been oxidised to phosphate.

Example 11

The product of Example 1 was tested against sodium phosphonosuccinate, a mixture of equal parts by weight sodium phosphosuccinate and sodium polymaleate, PTCB and HPP in corrosion inhibition tests "calcium only" (Test Method No 3 above) and "zinc only" (Test Method No 4 above). The results in mm/yr are recorded in Table 2.

TABLE 2

| Inhibitor | Ca++ 3.5 hrs | Ca++ 20 hrs | Zn++ 3.5 hrs | Zn++ 20 hrs |
|---|---|---|---|---|
| Blank | 0.270 | — | — | — |
| Sodium Phosphonosuccinate | 0.135 | — | — | — |
| Sodium Phosphonosuccinate and Sodium polymaleate | 0.069 | 0.068 | — | — |
| Example 1 | 0.048 | 0.020 | 0.021 | 0.020 |
| PTCB | 0.064 | 0.079 | — | — |
| HPP | 0.025 | 0.008 | 0.246 | 0.160 |

Example 12

The products of examples 1, 3 and 4 were compared using test methods 1, 2 and 3 (above). The results are reported in the following Table 3.

TABLE 3

| Inhibitor | Example 1 | Example 3 | Example 4 |
|---|---|---|---|
| Test No. 1 | 2.3 | 5–10 | 2.7–2.9 |
| Test No. 2 | 1.4 | 2.4–2.8 | 1.0–1.2 |
| Test No. 3 | | | |
| (i) after 3½ hours | 0.048 | 0.037 | 0.029 |
| (ii) after 20 hours | 0.02 | 0.03 | 0.021 |

Example 13

The product of Example 1 was found to give 100% inhibition of barium sulphate scale after 4 hours at a level of 50 ppm. in water at 90° C. containing 126 mg $l^{-1}$ barium ion and 1210 mg $l^{-1}$ sulphate ion at pH 6.5 (determined at 25° C.). The inhibition after 24 hours was 82%.

Example 14

A solution of propargyl alcohol (28 g, 0.5M), made up to 500 ml with water was added dropwise over 6 h to a stirred refluxing solution of phosphorous acid (82 g, 1.0M) and sodium hydroxide (80 g, 2.0M) in water (200 ml). The reaction was maintained under an atmosphere of nitrogen. During the addition period sodium persulphate (ca. 48 g) was added portionwise (about 8 g $h^{-1}$). A further 10 g of sodium persulphate was then added over about 0.5 h. Water (ca 500 ml) was added and about 500 ml was distilled from the reaction mixture to remove any propargyl alcohol as an azeotrope with water. The dark brown solution obtained was analysed by $^{31}P$ n.m.r. spectroscopy (in $D_2O$). The reaction consists of ca. 70 mol % organo-phosphorus compounds; the majority of which (ca. 80%) is 1,2-diphosphono 3-hydroxypropane. The remaining 30 mol % of phosphorus was ca. half oxidised to phosphate and half remained as unreacted phosphorous acid. $^{13}C$ n.m.r. data was consistent with the product outlined above.

Example 15

The product of example 14 was taken without purification and tested for scale and corrosion inhibition as follows:

(a) Scaling (Test Method 1)

The product of Example 14 provided 100% inhibition of aragonite scale at a concentration of 1.0-1.2 mg. $l^{-1}$ total active expressed as phosphonic acid.

This is sufficient to indicate commercial utility as a scale inhibitor.

(b) Corrosion Inhibitor (Test Method No. 3)

After a contact time of 3.5 hours the corrosion rate was measured at 0.043 mm/yr. After 20 hours the corrosion rate was measured as 0.029 mm/yr. This indicates potential commercial utility as corrosion inhibitor.

Corrosion inhibition has been observed at concentrations below 10 ppm, which correspond to the levels of HPP required. The novel compounds of the invention moreover retain their activity in chlorinated water systems, unlike HPP.

Example 16

In a field test, an open recirculating cooling water system in a chemical manufacturing plant was operating under the following conditions;

| | |
|---|---|
| rate of circulation | 120 m$^3$/hr |
| cooling tower inlet temp. | 33° C. |
| cooling tower outlet temp. | 25° C. (at 18.3° C. wet bulb) |
| heat load | 4 × 10$^6$ KJ/hr |
| make up water | 3600 kg/hr |
| blowdown | 2300 kg/hr |
| acid dose rate (36% HCl) | 0.313 Kg/hr |
| product of Example 1 (dose rate) | 0.72 Kg/hr |
| pH of Cooling water | 6.8 |
| conductivity | 1050 microsiemens |
| product of Example 1 (concentrations) | 55 mg l$^{-1}$ |
| calcium hardness | 260 mg l$^{-1}$ |
| total hardness | 340 mg l$^{-1}$ |
| chloride | 260 mg l$^{-1}$ |
| tolyltriazole (copper corrosion inhibitor | 1.0 mg l$^{-1}$ |

A continuous corrosion probe gave measurements of the corrosion between 0.025 and 0.076 mm per year. Coupons of mild steel and copper were suspended in the cooling water. After 25 days the coupons were retrieved and weighed. The steel coupon was found to have lost metal at a rate equivalent to 0.034 mm/year. The copper coupon lost metal at a rate equivalent to 7.6 × 10$^{-4}$ mm/yr.

The foregoing corrosion rate qualifies as "excellent" protection according the standard defined in "Cooling Water Treatment—a Code of Practice," P62, Appendix A4, Section L, published in 1982 by the Industrial Water Society.

Example 17

A solution of methacrylic acid (43 g, 0.5M) and sodium hydroxide (20 g, 0.5M) in water (300 ml) was added dropwise over 3 h to a stirred refluxing solution of phosphorous acid (13.7 g, 0.17M and sodium hydroxide (13.4 g, 0.33M) in water (100 ml). Sodium persulphate (23.8 g, 20 mol % w.r.t. the methacrylic acid) was added portionwise over this period. After this a further 0.5M of methacrylic acid and 20 mol % of sodium persulphate were added in a like manner. A $^{31}$P n.m.r. spectrum indicated that ca. 61% of the phosphorous acid had reacted to give organophosphorus materials. $^{13}$C n.m.r. indicated that all the methacrylic acid had reacted and therefore that the resulting product contains on average 10 methacrylate units to each phosphorus.

Example 18

A solution of butyn-1,4-diol (10.8 g, 0.125M) in water (200 ml) was added dropwise over 5 h to a stirred refluxing solution of phosphorous acid (20.55 g, 0.25M) and sodium hydroxide (20 g, 01.5M in water (100 ml). Over this period a solution of sodium persulphate (11.9 g) in water (130 ml) was added simultaneously. A $^{31}$P n.m.r spectrum of this reaction mixture indicated that ca. 11% of the phosphorous acid had been converted to organophosphorus compounds.

Example 19

A solution of acetylene dicarboxylic acid (mono potassium salt) (50 g, 0.329M) and sodium hydroxide (13.2 g, 0.329M) in water (150 ml) was added dropwise over 5 h to a stirred refluxing solution of phosphorous acid (53.9 g, 0.658M) and sodium hydroxide (52.6 g, 1.316M) in water (200 ml). Over a period of 6 h (starting at the same time as the acetylene dicarboxylic acid addition) a solution of sodium persulphate (31.3 g) in water (130 ml) was also added.

A $^{31}$P n.m.r. spectrum of the reaction mixture indicated that ca. 30 mol % of the phosphorous acid had reacted to give organophosphorus compounds.

Example 20

A solution of acetylene carboxylic acid (10.1 g, 0.144M) and sodium hydroxide (5.8 g, 0.144M) in water (200 ml) was added dropwise over 5.5 h to a stirred refluxing solution of phosphorus acid (23.66 g, 0.288M) and sodium hydroxide (23.0 g, 0.575M) in water (150 ml). A solution of sodium persulphate (13.7 g) in water (130 ml) was also added simultaneously over this period. The reaction mixture obtained was studied by $^{31}$P and $^{13}$C n.m.r. spectroscopy. This indicated that ca. 85 mol % of the phosphorous acid had reacted to give organophosphorus compounds and 12 mol % had been oxidised to phosphate. The main organophosphorus component (which contained ca. 50 mol % of the reacted phosphorus) was 2,3-diphosphonopropanoic acid. No acetylene carboxylic acid remained unreacted.

Example 21

A solution of maleic acid (58 g, 0.5M), phosphorous acid (41 g, 0.5M), and sodium hydroxide (80 g 2M) in water (300 ml) was evaporated in vacuo until a ca. 75% w/w solids/25% w/w water mixture was obtained. This mixture was heated (temperature maintained between 110° and 120° C.) and stirred under an atmosphere of nitrogen. Over a period of 1 h a solution of sodium persulphate (6 g), 5 mol % w.r.t. the maleate) in water (50 ml) was added dropwise. ca. 10 g of water was also distilled out of the reaction mixture during this period. After the addition the reaction mixture was allowed to cool to give a viscous clear oil. $^{31}$P n.m.r. spectroscopic analysis indicated that 82% of the phosphite had reacted to give organophosphorus material.

Example 22

A solution of maleic acid (116 g, 1.0M), phosphorous acid (63.1 g 0.77M) and sodium hydroxide (301 g of a 47% w/w solution) in water (230 ml) was heated to reflux and water distilled from the reaction mixture until a mixture that contained 30% water was obtained. Hydrogen peroxide (19.4 g of a 35% solution) was added then dropwise over 1 hour to the stirred refluxing mixture. An exothermic reaction was observed after which the reaction mixture was diluted with water to obtain a ca. 5% solution. $^{31}P$ n.m.r. spectroscopy of the reaction mixture indicated that ca. 96 mol % of the phosphorous acid had reacted to give organophosphorus materials. $^{13}C$ n.m.r. data indicated that >95% of the maleic acid has reacted.

The product was analyzed by ion chromatography using a "DIONEX" (Registered Trade Mark) 4401 ion chromatograph equipped with a gradient pump, conductivity detector of sensitivity 30 us, UV detector (wavelength 215 mm, sensitivity 1.0 aufs) anion membrane suppressor and column oven, with AS5a analytical column and AG5a guard column, employing the following concentration gradient:

|  | % H$_2$O | % 400 mM Na OH |
|---|---|---|
| Initial | 95 | 5 |
| 20 mins | 50 | 50 |
| 30 mins | 50 | 50 |

The run time was 30 mins. at a flow rate of 1.0 ml/min, regenerant flow 4.0 ml/min, column temperature 40° C. and sample concentration 50 mg in 50 ml H$_2$O.

The analysis showed peaks inter alia at 8.82 mins, 12.65 mins, 16.65 mins, 17.68 mins, and 18.77 mins (see FIG. 1). The peak at 8.82 mins has been positively identified as due to phosphate and that at 12.65 mins as phosphonosuccinate. The peaks at 16.65, 17.68 and 18.77 are attributed to different diastereomers of the phosphonated dimer.

(i) Separation of high molecular weight material from Example 22

A sample of the material described in Example 22 was converted to the free acid by precipitation/filtration of sodium chloride with excess conc. HCl and methanol. After removal of the excess HCl by evaporation, an aqueous solution of the remaining material was stirred with an ion exchange resin (Amberlite resin IR-120(H) 0.3–1.18 mm) to remove as much residual sodium as possible. This material was freeze dried and then boiled with a large excess of trimethylorthoformate until no further methylation was observed (by phosphorus n.m.r.). Evaporation of the excess trimethylorthoformate yielded a dark brown oil which was high vacuum distilled (max. head temp. was 155 degrees at ca. 3 mmHg). This yielded 42.2 g of distilled material (phosphorus n.m.r. spectroscopy indicated that this material was tetramethylphosphonosuccinate with a small amount of trimethylphosphate) from 67.7 g of methylated material. The undistilled dark brown/black residue was added to conc. HCl and boiled for 5 hours. Treatment with activated charcoal, filtration and then evaporation of the filtrate yielded 10.7 g of a solid yellow material.

Example 23

Sodium hydroxide (262.1 g of a 47% w/w solution, 3.08M) was added dropwise to a solution of phosphorous acid (116.3 g, 1.54M) in water (415 ml). After this addition maleic anhydride (196 g, 2.0M) was added slowly over 0.5 hours then a further 340.4 g of sodium hydroxide (47% w/w, 4M) was added dropwise followed by a further 15 ml of water. The reaction mixture was adjusted to ca. pH 9 with sodium hydroxide and then water (600 g) was distilled from the mixture to obtain a ca. 68% solids solution. Hydrogen peroxide (9.7 g of a 35% solution) was then added over 1.5 hours to the stirred refluxing reaction mixture. The mixture was further refluxed for 0.25 hours and then, after cooling, water (ca. 270 ml) was added to obtain a ca. 50% solution. Phosphorus n.m.r. spectroscopy indicated that ca. 95 mol % of the phosphorous acid had reacted to give organophosphorus material and the remainder had been oxidized to phosphate.

Example 24

Prepared Using a 50% Heel

A solution of maleic acid (58 g, 0.5M), phosphorous acid (31.6 g, 0.39M), sodium hydroxide (150.2 g of a 47% solution), 257 g of a 50% solution of Example One (adjusted to pH 9.0 and ca. 92% pure by phosphorus n.m.r. spectroscopy) and water (115 ml) was heated to reflux and 245 g of water distilled out to obtain a ca. 70% solids solution. To this stirred refluxing mixture hydrogen peroxide (5–6 mol % w.r.t. maleate) was added over 20 mins. The reaction mixture was then cooled. Phosphorus n.m.r. spectroscopy indicated a total yield of 94% of organophosphorus material.

Example 25

Prepared Via a Semicontinuous Method 184 g of a 70% solution of the material prepared in Example 22 was heated to reflux. Over a period of 1 hour 40 min. a solution of maleic acid (58 g, 0.5N), phosphorous acid (31.6 g, 0.39M), sodium hydroxide (150.5 g of a 47% solution) in water (115 ml) was added dropwise. Simultaneously, hydrogen peroxide (4.8 g of a 35% solution) was added and water (177 g) was distilled out over the addition period. After the additions a further 1.5 g of hydrogen peroxide was added dropwise over 20 mins to the refluxing reaction mixture. Phosphorus n.m.r. spectroscopy indicated a ca. 92 mol % yield of organophosphorus material.

Example 26

Demonstrating Synergism

The separated phosphonated dimer product of Example 22 was mixed with sodium phosphonosuccinate in varying proportions. Each of the mixtures was subjected to a calcium corrosion inhibition test (120 ppm. Ca$^{++}$, 60 ppm total inhibitor, pH 7.5, 25° C.).

The results are plotted in FIG. 2 wherein the horizontal axis is the percentage of dimer by weight based on the weight of the mixture of dimer and monomer, and the vertical axis is corrosion rate measured after 20 hours and expressed in millimeters per year. The figures shown on the plotted points are the concentration of dimer in ppm. Thus the first point on the vertical axis is the corrosion rate in the presence of 60 parts per million of the monomer, in the absence of any dimer, and the last point labelled 60 represents the corrosion rate with 60 parts per million of the dimer in the absence of any monomer. In the absence of synergism the plot should be the dashed straight line shown in FIG. 2, joining these two points. Anything below that line is evidence of synergism. Thus practically all compositions up to about 99% dimer are synergistic. It is noted that the compositions containing 5, 10, 20 and 30 parts per million of the dimer all give less corrosion than either the monomer or the dimer alone. Thus 60 parts per million of the dimer gives approximately half the corrosion observed with 60 parts per million of monomer and 10 parts per million of dimer gives substantially less corrosion than the composition with 60 parts per million of dimer. Also, as shown in FIG. 2, all dimer compositions from about 8% to about 99% have synergistic corrosion rates of less than about 0.05 millimeters per year.

The present disclosure describes the embodiments of the present invention which include one or a plurality of elements and/or method steps which comprise the embodiments of the invention. Embodiments of the invention also (i) consist of and (ii) consist essentially of, the described element (s) and/or method steps.

We claim:
1. 2,3-diphosphonopropan-1-ol and its salts.
2. 2,3-diphosphonabuta-1,4-diol and its salts.
3. Phosphonated dimer of maleic anhydride.

* * * * *